US011452763B2

(12) United States Patent
Brody et al.

(10) Patent No.: US 11,452,763 B2
(45) **Date of Patent: *Sep. 27, 2022**

(54) THERAPEUTIC PEGYLATED GROWTH HORMONE ANTAGONISTS

(71) Applicant: Molecular Technologies Laboratories LLC, Galena, OH (US)

(72) Inventors: Richard S. Brody, Galena, OH (US); Thomas J. Zupancic, Powell, OH (US); John J. Kopchick, Athens, OH (US); Reetobrata Basu, Athens, OH (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/903,644

(22) Filed: Jun. 17, 2020

(65) Prior Publication Data

US 2020/0390863 A1 Dec. 17, 2020

Related U.S. Application Data

(60) Provisional application No. 62/862,222, filed on Jun. 17, 2019.

(51) Int. Cl.

| | |
|---|---|
| ***A61K 38/27*** | (2006.01) |
| ***A61K 47/60*** | (2017.01) |
| ***A61P 35/00*** | (2006.01) |
| ***C07K 14/61*** | (2006.01) |
| ***C07K 19/00*** | (2006.01) |

(52) U.S. Cl.

CPC .............. *A61K 38/27* (2013.01); *A61K 47/60* (2017.08); *C07K 14/61* (2013.01); *C07K 19/00* (2013.01)

(58) Field of Classification Search

CPC ......... A61K 38/27; A61K 47/60; A61P 35/00; C07K 14/61; C07K 19/00

See application file for complete search history.

(56) References Cited

U.S. PATENT DOCUMENTS 7,399,839 B2 * 7/2008 Cox ..................... C07K 1/1133 530/350

7,947,473 B2 5/2011 Buechler et al.

8,778,880 B2 * 7/2014 Cho ....................... C07H 21/04 514/11.4

2009/0203589 A1 8/2009 Girard et al.

2019/0099497 A1 4/2019 Brody

FOREIGN PATENT DOCUMENTS

WO WO1997011178 A1 3/1997

OTHER PUBLICATIONS

Muller et al., "Growth Hormone Receptor Antagonists," The Journal of Clinical Endocrinology & Metabolism, 2004, 89(4): 1503-1511. (Year: 2004).*

SOMAVERT from RxList, pp. 1-43. Accessed on Jan. 20, 2022. (Year: 2022).*

Copenheaver, Blaine R.; PCT International Search Report for PCT/US2020/038079; dated Oct. 6, 2020; 3 pages.

Wang et al. "Disruption of Growth Hormone Signaling Retards Prostate Carcinogenesis in the Probasin/TAg Rat," Endocrinology, Mar. 1, 2008 (Mar. 1, 2008), vol. 149, Iss. 3, pp. 1366-1376, entire document.

Eijnden et al. "Disulfide bonds determine growth hormone receptor folding, dimerisation and ligand binding " Journal of Cell Science, Jul. 4, 2006 (Jul. 4, 2006), vol. 119, Iss. 15, pp. 3078-3086, entire document.

* cited by examiner

*Primary Examiner* — Julie Ha

(57) ABSTRACT

Growth hormone receptor antagonists, comprising human growth hormone receptor antagonist G120K, wherein one amino acid of human growth hormone receptor antagonist G120K has been mutated to cysteine or wherein two amino acids of human growth hormone receptor antagonist G120K have been mutated to cysteine, and wherein the one amino acid mutated to cysteine is T142, and wherein the two amino acids mutated to cysteine are T142 and H151; and a polyethylene glycol molecule conjugated to each substituted cysteine in the human growth hormone receptor antagonist G120K mutant. These growth hormone receptor antagonists are useful in treating diseases or conditions, such as cancer and acromegaly, that are responsive to human growth hormone receptor antagonists.

7 Claims, 9 Drawing Sheets

Specification includes a Sequence Listing.

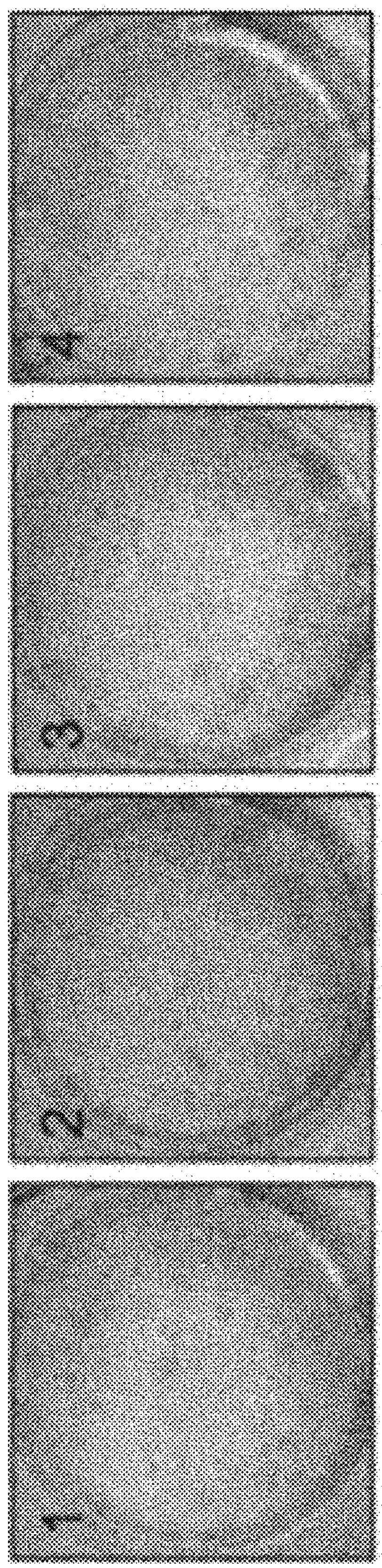
FIG. 7A
FIG. 7B
FIG. 7C
FIG. 7D
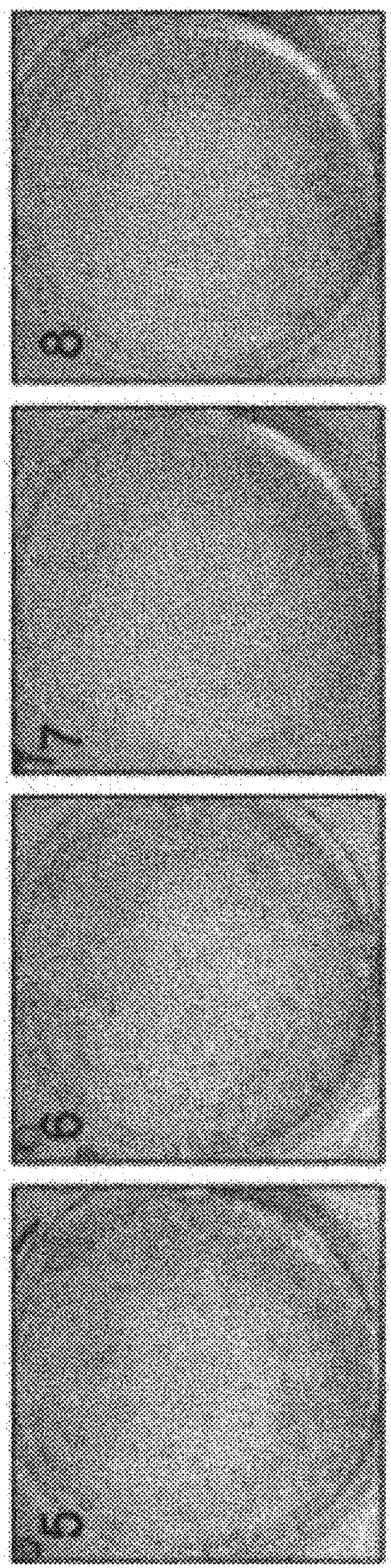
FIG. 7E
FIG. 7F
FIG. 7G
FIG. 7H

SEQUENCE LISTING

<160> NUMBER OF SEQ ID NOS: 24

<210> SEQ ID NO 1
<211> LENGTH: 567
<212> TYPE: DNA
<213> ORGANISM: Artificial Sequence
<220> FEATURE:

```
<223> OTHER INFORMATION: WThGH (DNA) Human Growth Hormone

<400> SEQUENCE: 1

ttcccaacca ttcccttatc caggcttttt gacaacgcta tgctccgcgc catcgtctgc     60

accagctggc ctttgacacc taccaggagt ttgaagaagc ctatatccca aggaacagaa    120

gtattcattc ctgcagaacc cccagacctc cctctgtttc tcagagtcat tccgacaccc    180

tccaacaggg aggaaacaca acagaaatcc aacctagagc tgctccgatc tccctgctgc    240

tcatccagtc gtggctggag cccgtgcagt tcctcaggag tgtcttgcca acagcctggt    300

gtacggcgcc tctgacagca acgtctatga cctcctaaag gacctgagga aggcatccaa    360

acgctgatgg ggaggctgga agatggcagc cccccggactg ggcaatcttc aagcagacct    420

acagcaagtt cgacacaaac tcacacaacg atgacgcact actaagaact acgggctgct    480

ctactgcttc aggaaggaca tggacaaggt cgagacattc ctcgcatcgt gcagtgccgc    540

tctgtggagg gcagctgtgg cttctag                                        567


<210> SEQ ID NO 2
<211> LENGTH: 188
<212> TYPE: PRT
<213> ORGANISM: Artificial Sequence
<220> FEATURE:
<223> OTHER INFORMATION: WThGH (amino acid) Human Growth Hormone
      (Mature Form)

<400> SEQUENCE: 2

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Leu Cys Phe Ser Glu Ser Ile Pro Thr Pro Ser Asn Arg Glu
    50                  55                  60

Glu Thr Gln Gln Lys Ser Asn Leu Glu Leu Leu Arg Ile Ser Leu Leu
65                  70                  75                  80

Leu Ile Gln Ser Trp Leu Glu Pro Val Gln Phe Leu Arg Ser Val Phe
                85                  90                  95

Ala Asn Ser Leu Val Tyr Gly Ala Ser Asp Ser Asn Val Asp Leu Leu
            100                 105                 110

Lys Asp Leu Glu Glu Gly Ile Gln Thr Leu Met Gly Arg Leu Glu Asp
        115                 120                 125

Gly Ser Pro Arg Thr Gly Gln Ile Phe Lys Gln Thr Tyr Ser Lys Phe
    130                 135                 140

Asp Thr Asn Ser His Asn Asp Asp Ala Leu Leu Lys Asn Tyr Gly Leu
145                 150                 155                 160

Leu Tyr Cys Phe Arg Lys Asp Met Lys Val Glu Thr Phe Leu Arg Ile
                165                 170                 175

Val Gln Cys Arg Ser Val Glu Gly Ser Cys Gly Phe
            180                 185


<210> SEQ ID NO 3
<211> LENGTH: 567
<212> TYPE: DNA
<213> ORGANISM: Artificial Sequence
<220> FEATURE:
<223> OTHER INFORMATION: G120K (DNA) Human Growth Hormone Antagonist
      G120K
```

<400> SEQUENCE: 3

```
ttcccaacca ttcccttatc caggcttttt gacaacgcta tgctccgcgc catcgtctgc     60
accagctggc ctttgacacc taccaggagt ttgaagaagc ctatatccca aggaacagaa    120
gtattcattc ctgcagaacc cccagacctc cctctgtttc tcagagtcat tccgacaccc    180
tccaacaggg aggaaacaca acagaaatcc aacctagagc tgctccgatc tccctgctgc    240
tcatccagtc gtggctggag cccgtgcagt tcctcaggag tgtcttgcca acagcctggt    300
gtacggcgcc tctgacagca acgtctatga cctcctaaag gacctgagga aaagatccaa    360
acgctgatgg ggaggctgga agatggcagc cccggactg ggcaatcttc aagcagacct     420
acagcaagtt cgacacaaac tcacacaacg atgacgcact actaagaact acgggctgct    480
ctactgcttc aggaaggaca tggacaaggt cgagacattc ctcgcatcgt gcagtgccgc    540
tctgtggagg gcagctgtgg cttctag                                        567
```

<210> SEQ ID NO 4
<211> LENGTH: 188
<212> TYPE: PRT
<213> ORGANISM: Artificial Sequence
<220> FEATURE:
<223> OTHER INFORMATION: G120K (amino acid) Human Growth Hormone Antagonist G120K (Mature Form)

<400> SEQUENCE: 4

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Leu Cys Phe Ser Glu Ser Ile Pro Thr Pro Ser Asn Arg Glu
    50                  55                  60

Glu Thr Gln Gln Lys Ser Asn Leu Glu Leu Leu Arg Ile Ser Leu Leu
65                  70                  75                  80

Leu Ile Gln Ser Trp Leu Glu Pro Val Gln Phe Leu Arg Ser Val Phe
                85                  90                  95

Ala Asn Ser Leu Val Tyr Gly Ala Ser Asp Ser Asn Val Asp Leu Leu
            100                 105                 110

Lys Asp Leu Glu Glu Lys Ile Gln Thr Leu Met Gly Arg Leu Glu Asp
        115                 120                 125

Gly Ser Pro Arg Thr Gly Gln Ile Phe Lys Gln Thr Tyr Ser Lys Phe
    130                 135                 140

Asp Thr Asn Ser His Asn Asp Asp Ala Leu Leu Lys Asn Tyr Gly Leu
145                 150                 155                 160

Leu Tyr Cys Phe Arg Lys Asp Met Lys Val Glu Thr Phe Leu Arg Ile
                165                 170                 175

Val Gln Cys Arg Ser Val Glu Gly Ser Cys Gly Phe
            180                 185
```

<210> SEQ ID NO 5
<211> LENGTH: 645
<212> TYPE: DNA
<213> ORGANISM: Artificial Sequence
<220> FEATURE:
<223> OTHER INFORMATION: G120K-T3C (DNA) Synthetic Constructs / Mutant Human Growth Hormone Antagonist

<400> SEQUENCE: 5

```
atggcgcatc accaccacca tcacggcagc agcggcgaga acctgtactt ccagggtgga     60

agctcgggat tcccatgcat tcccttatcc aggctttttg acaacgctat gctccgcgcc    120

catcgtctgc accagctggc ctttgacacc taccaggagt ttgaagaagc ctatatccca    180

aaggaacaga agtattcatt cctgcagaac ccccagacct ccctctgttt ctcagagtct    240

attccgacac cctccaacag ggaggaaaca caacagaaat ccaacctaga gctgctccgc    300

atctccctgc tgctcatcca gtcgtggctg gagcccgtgc agttcctcag gagtgtcttc    360

gccaacagcc tggtgtacgg cgcctctgac agcaacgtct atgacctcct aaaggaccta    420

gaggaaaaga tccaaacgct gatggggagg ctggaagatg gcagcccccg gactgggcag    480

atcttcaagc agacctacag caagttcgac acaaactcac acaacgatga cgcactactc    540

aagaactacg ggctgctcta ctgcttcagg aaggacatgg acaaggtcga gacattcctg    600

cgcatcgtgc agtgccgctc tgtggagggc agctgtggct tctag                    645
```

<210> SEQ ID NO 6
<211> LENGTH: 214
<212> TYPE: PRT
<213> ORGANISM: Artificial Sequence
<220> FEATURE:
<223> OTHER INFORMATION: G120K-T3C (amino acid) Synthetic Constructs / Mutant Human Growth Hormone Antagonists

<400> SEQUENCE: 6

```
Met Ala His His His His His His Gly Ser Ser Gly Glu Asn Leu Tyr
1               5                   10                  15

Phe Gln Gly Gly Ser Ser Gly Phe Pro Cys Ile Pro Leu Ser Arg Leu
            20                  25                  30

Phe Asp Asn Ala Met Leu Arg Ala His Arg Leu His Gln Leu Ala Phe
        35                  40                  45

Asp Thr Tyr Gln Glu Phe Glu Glu Ala Tyr Ile Pro Lys Glu Gln Lys
    50                  55                  60

Tyr Ser Phe Leu Gln Asn Pro Gln Thr Ser Leu Cys Phe Ser Glu Ser
65                  70                  75                  80

Ile Pro Thr Pro Ser Asn Arg Glu Glu Thr Gln Gln Lys Ser Asn Leu
                85                  90                  95

Glu Leu Leu Arg Ile Ser Leu Leu Leu Ile Gln Ser Trp Leu Glu Pro
            100                 105                 110

Val Gln Phe Leu Arg Ser Val Phe Ala Asn Ser Leu Val Tyr Gly Ala
        115                 120                 125

Ser Asp Ser Asn Val Tyr Asp Leu Leu Lys Asp Leu Glu Glu Lys Ile
    130                 135                 140

Gln Thr Leu Met Gly Arg Leu Glu Asp Gly Ser Pro Arg Thr Gly Gln
145                 150                 155                 160

Ile Phe Lys Gln Thr Tyr Ser Lys Phe Asp Thr Asn Ser His Asn Asp
                165                 170                 175

Asp Ala Leu Leu Lys Asn Tyr Gly Leu Leu Tyr Cys Phe Arg Lys Asp
            180                 185                 190

Met Asp Lys Val Glu Thr Phe Leu Arg Ile Val Gln Cys Arg Ser Val
        195                 200                 205

Glu Gly Ser Cys Gly Phe
    210
```

<210> SEQ ID NO 7

<211> LENGTH: 645
<212> TYPE: DNA
<213> ORGANISM: Artificial Sequence
<220> FEATURE:
<223> OTHER INFORMATION: G120K-E39C (DNA) Synthetic Constructs / Mutant Human Growth Hormone Antagnonist

<400> SEQUENCE: 7
atggcgcatc accaccacca tcacggcagc agcggcgaga acctgtactt ccagggtgga 60
agctcgggat tcccaaccat tcccttatcc aggctttttg acaacgctat gctccgcgcc 120
catcgtctgc accagctggc ctttgacacc taccaggagt ttgaagaagc ctatatccca 180
aagtgccaga agtattcatt cctgcagaac ccccagacct ccctctgttt ctcagagtct 240
attccgacac cctccaacag ggaggaaaca caacagaaat ccaacctaga gctgctccgc 300
atctccctgc tgctcatcca gtcgtggctg gagcccgtgc agttcctcag gagtgtcttc 360
gccaacagcc tggtgtacgg cgcctctgac agcaacgtct atgacctcct aaaggaccta 420
gaggaaaaga tccaaacgct gatggggagg ctggaagatg gcagcccccg gactgggcag 480
atcttcaagc agacctacag caagttcgac acaaactcac acaacgatga cgcactactc 540
aagaactacg ggctgctcta ctgcttcagg aaggacatgg acaaggtcga gacattcctg 600
cgcatcgtgc agtgccgctc tgtggagggc agctgtggct tctag 645

<210> SEQ ID NO 8
<211> LENGTH: 214
<212> TYPE: PRT
<213> ORGANISM: Artificial Sequence
<220> FEATURE:
<223> OTHER INFORMATION: G120K-E39C (amino acid) Synthetic Constructs / Mutant Human Growth Hormone Antagonists

<400> SEQUENCE: 8

Met Ala His His His His His His Gly Ser Ser Gly Glu Asn Leu Tyr
1 5 10 15

Phe Gln Gly Gly Ser Ser Gly Phe Pro Thr Ile Pro Leu Ser Arg Leu
20 25 30

Phe Asp Asn Ala Met Leu Arg Ala His Arg Leu His Gln Leu Ala Phe
35 40 45

Asp Thr Tyr Gln Glu Phe Glu Glu Ala Tyr Ile Pro Lys Cys Gln Lys
50 55 60

Tyr Ser Phe Leu Gln Asn Pro Gln Thr Ser Leu Cys Phe Ser Glu Ser
65 70 75 80

Ile Pro Thr Pro Ser Asn Arg Glu Glu Thr Gln Gln Lys Ser Asn Leu
85 90 95

Glu Leu Leu Arg Ile Ser Leu Leu Leu Ile Gln Ser Trp Leu Glu Pro
100 105 110

Val Gln Phe Leu Arg Ser Val Phe Ala Asn Ser Leu Val Tyr Gly Ala
115 120 125

Ser Asp Ser Asn Val Tyr Asp Leu Leu Lys Asp Leu Glu Glu Lys Ile
130 135 140

Gln Thr Leu Met Gly Arg Leu Glu Asp Gly Ser Pro Arg Thr Gly Gln
145 150 155 160

Ile Phe Lys Gln Thr Tyr Ser Lys Phe Asp Thr Asn Ser His Asn Asp
165 170 175

Asp Ala Leu Leu Lys Asn Tyr Gly Leu Leu Tyr Cys Phe Arg Lys Asp
180 185 190

Met Asp Lys Val Glu Thr Phe Leu Arg Ile Val Gln Cys Arg Ser Val

```
        195                 200                 205

Glu Gly Ser Cys Gly Phe
    210


<210> SEQ ID NO 9
<211> LENGTH: 645
<212> TYPE: DNA
<213> ORGANISM: Artificial Sequence
<220> FEATURE:
<223> OTHER INFORMATION: G120K-P48C (DNA) Synthetic Constructs / Mutant
      Human Growth Hormone Antagonists

<400> SEQUENCE: 9

atggcgcatc accaccacca tcacggcagc agcggcgaga acctgtactt ccagggtgga     60

agctcgggat tcccaaccat tcccttatcc aggctttttg acaacgctat gctccgcgcc    120

catcgtctgc accagctggc ctttgacacc taccaggagt ttgaagaagc ctatatccca    180

aaggaacaga agtattcatt cctgcagaac tgtcagacct ccctctgttt ctcagagtct    240

attccgacac cctccaacag ggaggaaaca caacagaaat ccaacctaga gctgctccgc    300

atctccctgc tgctcatcca gtcgtggctg gagcccgtgc agttcctcag gagtgtcttc    360

gccaacagcc tggtgtacgg cgcctctgac agcaacgtct atgacctcct aaaggaccta    420

gaggaaaaga tccaaacgct gatggggagg ctggaagatg gcagcccccg gactgggcag    480

atcttcaagc agacctacag caagttcgac acaaactcac acaacgatga cgcactactc    540

aagaactacg ggctgctcta ctgcttcagg aaggacatgg acaaggtcga gacattcctg    600

cgcatcgtgc agtgccgctc tgtggagggc agctgtggct tctag                    645


<210> SEQ ID NO 10
<211> LENGTH: 70
<212> TYPE: PRT
<213> ORGANISM: Artificial Sequence
<220> FEATURE:
<223> OTHER INFORMATION: G120K-P48C (amino acid) Synthetic Constructs /
      Mutant Human Growth Hormone Antagonists

<400> SEQUENCE: 10

Gln Thr Leu Met Gly Arg Leu Glu Asp Gly Ser Pro Arg Thr Gly Gln
1               5                   10                  15

Ile Phe Lys Gln Thr Tyr Ser Lys Phe Asp Thr Asn Ser His Asn Asp
            20                  25                  30

Asp Ala Leu Leu Lys Asn Tyr Gly Leu Leu Tyr Cys Phe Arg Lys Asp
        35                  40                  45

Met Asp Lys Val Glu Thr Phe Leu Arg Ile Val Gln Cys Arg Ser Val
    50                  55                  60

Glu Gly Ser Cys Gly Phe
65                  70


<210> SEQ ID NO 11
<211> LENGTH: 645
<212> TYPE: DNA
<213> ORGANISM: Artificial Sequence
<220> FEATURE:
<223> OTHER INFORMATION: G120K-Q69C (DNA) Synthetic Constructs / Mutant
      Human Growth Hormone Antagonists

<400> SEQUENCE: 11

atggcgcatc accaccacca tcacggcagc agcggcgaga acctgtactt ccagggtgga     60

agctcgggat tcccaaccat tcccttatcc aggctttttg acaacgctat gctccgcgcc    120
```

```
catcgtctgc accagctggc ctttgacacc taccaggagt ttgaagaagc ctatatccca    180

aaggaacaga agtattcatt cctgcagaac ccccagacct ccctctgttt ctcagagtct    240

attccgacac cctccaacag ggaggaaaca cagtgcaaat ccaacctaga gctgctccgc    300

atctccctgc tgctcatcca gtcgtggctg gagcccgtgc agttcctcag gagtgtcttc    360

gccaacagcc tggtgtacgg cgcctctgac agcaacgtct atgacctcct aaaggaccta    420

gaggaaaaga tccaaacgct gatggggagg ctggaagatg gcagcccccg gactgggcag    480

atcttcaagc agacctacag caagttcgac acaaactcac acaacgatga cgcactactc    540

aagaactacg ggctgctcta ctgcttcagg aaggacatgg acaaggtcga gacattcctg    600

cgcatcgtgc agtgccgctc tgtggagggc agctgtggct tctag                    645


<210> SEQ ID NO 12
<211> LENGTH: 214
<212> TYPE: PRT
<213> ORGANISM: Artificial Sequence
<220> FEATURE:
<223> OTHER INFORMATION: G120K-Q69C (amino acid) Synthetic Constructs /
      Mutant Human Growth Hormone Antagonists

<400> SEQUENCE: 12

Met Ala His His His His His His Gly Ser Ser Gly Glu Asn Leu Tyr
1               5                   10                  15

Phe Gln Gly Gly Ser Ser Gly Phe Pro Thr Ile Pro Leu Ser Arg Leu
            20                  25                  30

Phe Asp Asn Ala Met Leu Arg Ala His Arg Leu His Gln Leu Ala Phe
        35                  40                  45

Asp Thr Tyr Gln Glu Phe Glu Glu Ala Tyr Ile Pro Lys Glu Gln Lys
    50                  55                  60

Tyr Ser Phe Leu Gln Asn Pro Gln Thr Ser Leu Cys Phe Ser Glu Ser
65                  70                  75                  80

Ile Pro Thr Pro Ser Asn Arg Glu Glu Thr Gln Cys Lys Ser Asn Leu
                85                  90                  95

Glu Leu Leu Arg Ile Ser Leu Leu Leu Ile Gln Ser Trp Leu Glu Pro
            100                 105                 110

Val Gln Phe Leu Arg Ser Val Phe Ala Asn Ser Leu Val Tyr Gly Ala
        115                 120                 125

Ser Asp Ser Asn Val Tyr Asp Leu Leu Lys Asp Leu Glu Glu Lys Ile
    130                 135                 140

Gln Thr Leu Met Gly Arg Leu Glu Asp Gly Ser Pro Arg Thr Gly Gln
145                 150                 155                 160

Ile Phe Lys Gln Thr Tyr Ser Lys Phe Asp Thr Asn Ser His Asn Asp
                165                 170                 175

Asp Ala Leu Leu Lys Asn Tyr Gly Leu Leu Tyr Cys Phe Arg Lys Asp
            180                 185                 190

Met Asp Lys Val Glu Thr Phe Leu Arg Ile Val Gln Cys Arg Ser Val
        195                 200                 205

Glu Gly Ser Cys Gly Phe
    210


<210> SEQ ID NO 13
<211> LENGTH: 576
<212> TYPE: DNA
<213> ORGANISM: Artificial Sequence
<220> FEATURE:
<223> OTHER INFORMATION: G120K-N99C (DNA) Synthetic Constructs / Mutant
      Human Growth Hormone Antagonists
```

<400> SEQUENCE: 13

```
ttcccaacca ttcccttatc caggcttttt gacaacgcta tgctccgcgc ccatcgtctg     60

caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgcctgcagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagacctaca gcaagttcga cacaaactca cacaacgatg acgcactact caagaactac    480

gggctgctct actgcttcag gaaggacatg gacaaggtcg agacattcct gcgcatcgtg    540

cagtgccgct ctgtggaggg cagctgtggc ttctag                              576
```

<210> SEQ ID NO 14
<211> LENGTH: 191
<212> TYPE: PRT
<213> ORGANISM: Artificial Sequence
<220> FEATURE:
<223> OTHER INFORMATION: G120K-N99C (amino acid) Synthetic Constructs / Mutant Human Growth Hormone Antagonists

<400> SEQUENCE: 14

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Cys Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 15
<211> LENGTH: 576
<212> TYPE: DNA
<213> ORGANISM: Artificial Sequence
<220> FEATURE:
<223> OTHER INFORMATION: T142C-GL2 (DNA) Synthetic Constructs / Mutant Human Growth Hormone Antagonists

<400> SEQUENCE: 15

```
ttcccaacca ttcccttatc caggcttttt gacaacgcta tgctccgcgc ccatcgtctg     60

caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgccaacagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagtgctaca gcaagttcga cacaaactca cacaacgatg acgcactact caagaactac    480

gggctgctct actgcttcag gaaggacatg gacaaggtcg agacattcct gcgcatcgtg    540

cagtgccgct ctgtggaggg cagctgtggc ttctag                              576
```

<210> SEQ ID NO 16
<211> LENGTH: 191
<212> TYPE: PRT
<213> ORGANISM: Artificial Sequence
<220> FEATURE:
<223> OTHER INFORMATION: T142C-GL2 (amino acid) Synthetic Constructs / Mutant Human Growth Hormone Antagonists

<400> SEQUENCE: 16

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Cys Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 17
<211> LENGTH: 576
<212> TYPE: DNA
<213> ORGANISM: Artificial Sequence
<220> FEATURE:
<223> OTHER INFORMATION: H151C-GL2 (amino acid) Synthetic Constructs / Mutant Human Growth Hormone Antagonists

<400> SEQUENCE: 17

```
ttcccaacca ttcccttatc caggcttttt gacaacgcta tgctccgcgc ccatcgtctg     60

caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgccaacagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagacctaca gcaagttcga cacaaactca tgcaacgatg acgcactact caagaactac    480

gggctgctct actgcttcag gaaggacatg gacaaggtcg agacattcct gcgcatcgtg    540

cagtgccgct ctgtggaggg cagctgtggc ttctag                              576
```

<210> SEQ ID NO 18
<211> LENGTH: 191
<212> TYPE: PRT
<213> ORGANISM: Artificial Sequence
<220> FEATURE:
<223> OTHER INFORMATION: H151C-GL2 (amino acid) Synthetic Constructs / Mutant Human Growth Hormone Antagonists

<400> SEQUENCE: 18

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser Cys Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 19
<211> LENGTH: 576
<212> TYPE: DNA
<213> ORGANISM: Artificial Sequence
<220> FEATURE:
<223> OTHER INFORMATION: G120K-N99C-dPEGX-H151C (DNA) Synthetic Constructs / Mutant Human Growth Hormone Antagonists

<400> SEQUENCE: 19

```
ttcccaacca ttcccttatc caggcttttt gacaacgcta tgctccgcgc ccatcgtctg     60

caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgcctgcagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagacctaca gcaagttcga cacaaactca tgcaacgatg acgcactact caagaactac    480

gggctgctct actgcttcag gaaggacatg gacaaggtcg agacattcct gcgcatcgtg    540

cagtgccgct ctgtggaggg cagctgtggc ttctag                              576
```

<210> SEQ ID NO 20
<211> LENGTH: 191
<212> TYPE: PRT
<213> ORGANISM: Artificial Sequence
<220> FEATURE:
<223> OTHER INFORMATION: G120K-N99C-dPEGX-H151C (amino acid) Synthetic Constructs / Mutant Human Growth Hormone Antagonists

<400> SEQUENCE: 20

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Cys Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser Cys Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 21
<211> LENGTH: 576
<212> TYPE: DNA
<213> ORGANISM: Artificial Sequence
<220> FEATURE:
<223> OTHER INFORMATION: N99C-T142C-dPEGA2 (DNA) Synthetic Constructs / Mutant Human Growth Hormone Antagonists

<400> SEQUENCE: 21

```
ttcccaacca ttcccttatc caggcttttt gacaacgcta tgctccgcgc ccatcgtctg     60
```

```
caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgcctgcagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagtgctaca gcaagttcga cacaaactca cacaacgatg acgcactact caagaactac    480

gggctgctct actgcttcag gaaggacatg gacaaggtcg agacattcct gcgcatcgtg    540

cagtgccgct ctgtggaggg cagctgtggc ttctag                              576
```

```
<210> SEQ ID NO 22
<211> LENGTH: 191
<212> TYPE: PRT
<213> ORGANISM: Artificial Sequence
<220> FEATURE:
<223> OTHER INFORMATION: N99C-T142C-dPEGA2 (amino acid) Synthetic
      Constructs / Mutant Human Growth Hormone Antagonists

<400> SEQUENCE: 22

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Cys Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Cys Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190


<210> SEQ ID NO 23
<211> LENGTH: 576
<212> TYPE: DNA
<213> ORGANISM: Artificial Sequence
<220> FEATURE:
<223> OTHER INFORMATION: G120K-H151C-T142C-dPEGA2 (DNA) Synthetic
      Constructs / Mutant Human Growth Hormone Antagonists

<400> SEQUENCE: 23

ttcccaacca ttcccttatc caggcttttt gacaacgcta tgctccgcgc ccatcgtctg     60
```

-continued

```
caccagctgg cctttgacac ctaccaggag tttgaagaag cctatatccc aaaggaacag    120

aagtattcat tcctgcagaa cccccagacc tccctctgtt tctcagagtc tattccgaca    180

ccctccaaca gggaggaaac acaacagaaa tccaacctag agctgctccg catctccctg    240

ctgctcatcc agtcgtggct ggagcccgtg cagttcctca ggagtgtctt cgccaacagc    300

ctggtgtacg gcgcctctga cagcaacgtc tatgacctcc taaaggacct agaggaaaag    360

atccaaacgc tgatggggag gctggaagat ggcagccccc ggactgggca gatcttcaag    420

cagtgctaca gcaagttcga cacaaactca tgcaacgatg acgcactact caagaactac    480

gggctgctct actgcttcag gaaggacatg gacaaggtcg agacattcct gcgcatcgtg    540

cagtgccgct ctgtggaggg cagctgtggc ttctag                              576


<210> SEQ ID NO 24
<211> LENGTH: 191
<212> TYPE: PRT
<213> ORGANISM: Artificial Sequence
<220> FEATURE:
<223> OTHER INFORMATION: G120K-H151C-T142C-dPEGA2 (amino acid) Synthetic
      Constructs / Mutant Human Growth Hormone Antagonists

<400> SEQUENCE: 24

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Lys Ile Gln Thr Leu Met Gly Arg Leu
        115                 120                 125

Glu Asp Gly Ser Pro Arg Thr Gly Gln Ile Phe Lys Gln Cys Tyr Ser
    130                 135                 140

Lys Phe Asp Thr Asn Ser Cys Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

THERAPEUTIC PEGYLATED GROWTH HORMONE ANTAGONISTS

CROSS-REFERENCE TO RELATED APPLICATIONS

This patent application claims the benefit of U.S. Provisional Patent Application Ser. No. 62/862,222 filed on Jun. 17, 2019 and entitled "Pegylated Growth Hormone Antagonists", the disclosure of which is hereby incorporated by reference herein in its entirety and made part of the present U.S. utility patent application for all purposes.

REFERENCE TO A SEQUENCE LISTING

A sequence listing in computer readable form (CRF) is on file. The sequence listing is in an ASCII text (.txt) file entitled SEQIDNOS_1_24_ST25.txt created on Jun. 11, 2020 and is 33 KB in size. The sequence listing is incorporated by reference as if fully recited herein.

BACKGROUND

The described invention relates in general to compositions for use as receptor antagonists, and more specifically to novel human growth hormone antagonists that have the potential to be highly effective therapeutics.

Human growth hormone, also known as somatotropin or somatropin, is a peptide hormone that stimulates growth, cell reproduction, and regeneration in humans and other animals. Growth hormone is a type of mitogen that is specific only to certain kinds of cells and is a 191-amino acid, single-chain polypeptide that is synthesized, stored, and secreted by somatotropic cells within the lateral wings of the anterior pituitary gland. Acromegaly is a syndrome that results when the anterior pituitary gland produces excess growth hormone (hGH) after epiphyseal plate closure at puberty. If hGH is produced in excess prior to epiphyseal plate closure, the result is gigantism (or giantism). A number of disorders may increase the pituitary's hGH output, although most commonly it involves a tumor called pituitary adenoma, derived from a distinct type of cell (somatotrophs). Acromegaly most commonly affects adults in middle age and can result in severe disfigurement, complicating conditions, and premature death if untreated. Because of its pathogenesis and slow progression, the disease is hard to diagnose in the early stages and is frequently missed for years until changes in external features, especially of the face, become noticeable.

A receptor is a protein molecule usually found embedded within the plasma membrane surface of a cell that receives chemical signals from outside the cell. When such chemical signals bind to a receptor, they cause some form of cellular/tissue response such as, for example, a change in the electrical activity of the cell. In this sense, a receptor is a protein molecule that recognizes and responds to endogenous chemical signals. An agonist, such as human growth hormone, is a chemical composition that binds to a receptor and activates the receptor to produce a biological response. Whereas an agonist causes an action, an antagonist blocks the action of the agonist and an inverse agonist causes an action opposite to that of the agonist. A receptor antagonist is a type of receptor ligand or drug that blocks or dampens agonist-mediated responses rather than provoking a biological response itself upon binding to a receptor. These compositions are sometimes called blockers and examples include alpha blockers, beta blockers, and calcium channel blockers. In pharmacology, antagonists have affinity but no efficacy for their cognate receptors, and binding will disrupt the interaction and inhibit the function of an agonist or inverse agonist at receptors. Antagonists mediate their effects by binding to the active (orthosteric) site or to other (allosteric) sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist-receptor binding. The majority of drug antagonists achieve their potency by competing with endogenous ligands or substrates at structurally defined binding sites on receptors. By definition, antagonists display no efficacy to activate the receptors they bind and antagonists do not maintain the ability to activate a receptor. Once bound, however, antagonists inhibit the function of agonists, inverse agonists, and partial agonists.

Growth hormone receptor antagonists such as the product SOMAVERT® (pegvisomant) are used in the treatment of acromegaly. Such compositions are used if the tumor of the pituitary gland causing the acromegaly cannot be controlled with surgery or radiation and the use of somatostatin analogues is unsuccessful. SOMAVERT® (pegvisomant) is typically delivered as a powder that is mixed with water and injected under the skin.

Pegylation is the process of both covalent and non-covalent amalgamation of polyethylene glycol (PEG) polymer chains to molecules and macrostructures, such as drugs, peptides, antibody fragments, or therapeutic proteins. Pegylation is routinely achieved by incubation of a reactive derivative of PEG with the target molecule and produces alterations in physiochemical properties, including changes in molecular size and molecular charge. These physical and chemical changes increase systemic retention of the therapeutic agent and can influence the binding affinity of the therapeutic moiety to the cell receptors and can alter the absorption and distribution patterns. The covalent attachment of PEG to a drug or therapeutic protein can also "mask" the agent from the host's immune system (i.e., reducing immunogenicity and antigenicity), and increase the hydrodynamic size (i.e., size in solution) of the agent which prolongs its circulatory time by reducing renal clearance. Pegylation can also provide water solubility to hydrophobic drugs and proteins.

Pegylation, by increasing the molecular weight of a molecule, can impart several significant pharmacological advantages over the unmodified form of the molecule, such as: (i) improved drug solubility; (ii) reduced dosage frequency, without diminished efficacy and with potentially reduced toxicity; (iii) extended circulating life; (iv) increased drug stability; and (v) enhanced protection from proteolytic degradation. PEGylated drugs also include the following commercial advantages: (i) opportunities for new delivery formats and dosing regimens; and (ii) extended patent life of previously approved drugs. PEG is a particularly attractive polymer for conjugation and the specific characteristics of PEG moieties relevant to pharmaceutical applications include: (i) water solubility; (ii) high mobility in solution; (iii) lack of toxicity and low immunogenicity; and (iv) altered distribution in the body.

The addition of high molecular weight polyethylene glycols (PEGs) to proteins has been previously shown to increase the in-vivo half-lives of these proteins by a size dependent decrease in elimination by the kidneys. The addition of PEGs also lowers the immunogenicity of the proteins and decreases aggregation and protease cleavage

[1]-[2]. Multiple known PEGylated proteins have been approved by the USFDA for therapeutic use, including hormones, cytokines, antibody fragments, and enzymes [1] and [3]-[4]. Thus, there is an ongoing need for the further development of PEGylated therapeutics, particularly for use in the treatment of diseases that are responsive to the use of human growth hormone (hGH) receptor antagonists or other receptor antagonists.

Evidence from human and animal studies supports a role for growth hormone (GH) in carcinogenesis. The level of growth hormone receptor (GHR) expression in 60 cancer cell lines from nine types of human cancer: breast, CNS, colon, leukemia, melanoma, non-small cell lung, ovarian, prostate, and renal has been determined [5]. High GHR expression levels were obtained for most of the cell lines for all of the cancer types except colon and leukemia. The GHR expression levels of the melanoma cell lines were exceptionally high, nearly fifty-fold higher than in the panel as a whole. Three melanoma cell types were treated with hGH and in two of the three hGH increased proliferation and induced activation of STATS and mTOR. The effects of GH and a siRNA mediated GHR knockdown cell line on tumor progression and epithelial mesenchymal transition in human melanoma cells has been investigated [6]. This research indicated that hGH promoted and GHR knockdown attenuated tumor proliferation, migration and invasion. The effect of GHR knockdown on the sensitivity of human melanoma cells to chemotherapy has been investigated [7]. This research indicated that hGH upregulates multiple ABC transporters, increasing the EC50 of the melanoma drug vemurafenib. GHR knockdown, in contrast, significantly increases drug retention by melanoma cells, decreases cell proliferation, and increases drug efficacy. Accordingly, the use of certain hGH antagonists as cancer therapeutics would be beneficial.

SUMMARY

The following provides a summary of certain example implementations of the disclosed inventive subject matter. This summary is not an extensive overview and is not intended to identify key or critical aspects or elements of the disclosed inventive subject matter or to delineate its scope. However, it is to be understood that the use of indefinite articles in the language used to describe and claim the disclosed inventive subject matter is not intended in any way to limit the described inventive subject matter. Rather the use of "a" or "an" should be interpreted to mean "at least one" or "one or more".

One implementation provides a first growth hormone receptor antagonist. This growth hormone receptor antagonist comprises human growth hormone receptor antagonist G120K, wherein one amino acid of human growth hormone receptor antagonist G120K has been mutated to cysteine or wherein two amino acids of human growth hormone receptor antagonist G120K have been mutated to cysteine, and wherein the one amino acid mutated to cysteine is T142, and wherein the two amino acids mutated to cysteine are T142 and H151; and a polyethylene glycol molecule conjugated to each substituted cysteine in the human growth hormone receptor antagonist G120K mutant. The polyethylene glycol molecule may contain a malemide group for conjugation to a free sulfhydryl group. The polyethylene glycol molecule conjugated to the one amino acid mutated to cysteine may be a polydispersed 40 kDa branched polyethylene glycol molecule. The polyethylene glycol molecules conjugated to the two amino acids mutated to cysteine may be two 40 kDa branched polyethylene glycol molecules, two 20 kDa branched polyethylene glycol molecules, two 20 kDa linear polyethylene glycol molecules, or two 4.5 kDa branched polyethylene glycols each containing three carboxylate anions. The human growth hormone receptor antagonist may be encoded by a DNA sequence having at least 95% identity to a DNA molecule selected from the group consisting of SEQ ID NOS: 15 and 23. The human growth hormone receptor antagonist has an amino acid sequence selected from the group consisting of SEQ ID NOS: 16 and 24. This implementation may also include a method for treating diseases or conditions responsive to human growth hormone receptor antagonists, comprising administering to the patient an effective amount of the described composition. The diseases or conditions may include cancers that express high levels of the growth hormone receptor; high levels of the prolactin receptor; or high levels of both the growth hormone receptor and the prolactin receptor. The cancers may include breast cancer, central nervous system cancer, melanoma, non-small cell lung cancer, ovarian cancer, prostate cancer, and renal cancer. This implementation may also include a variant wherein the following amino acids mutations have been made: H18D, H21N, R167N, K168A, D171S, K172R, E174S, and I179, and wherein these mutations are operative to prevent binding to a prolactin receptor. This variant may be used in a method for treating acromegaly, comprising administering to the patient an effective amount of the disclosed composition.

Another implementation provides a second growth hormone receptor antagonist. This growth hormone receptor antagonist comprises human growth hormone receptor antagonist G120K, wherein one amino acid of human growth hormone receptor antagonist G120K has been mutated to cysteine or wherein two amino acids of human growth hormone receptor antagonist G120K have been mutated to cysteine, and wherein the one amino acid mutated to cysteine is T142, and wherein the two amino acids mutated to cysteine are T142 and H151; and a polyethylene glycol molecule conjugated to each substituted cysteine in the human growth hormone receptor antagonist G120K mutant, herein the polyethylene glycol molecule conjugated to the one amino acid mutated to cysteine is a polydispersed 40 kDa branched polyethylene glycol molecule; and wherein the polyethylene glycol molecules conjugated to the two amino acids mutated to cysteine are two 40 kDa branched polyethylene glycol molecules, two 20 kDa branched polyethylene glycol molecules, two 20 kDa linear polyethylene glycol molecules, or two 4.5 kDa branched polyethylene glycols each containing three carboxylate anions. The polyethylene glycol molecule may contain a malemide group for conjugation to a free sulfhydryl group. The human growth hormone receptor antagonist may be encoded by a DNA sequence having at least 95% identity to a DNA molecule selected from the group consisting of SEQ ID NOS: 15 and 23. The human growth hormone receptor antagonist has an amino acid sequence selected from the group consisting of SEQ ID NOS: 16 and 24. This implementation may also include a method for treating diseases or conditions responsive to human growth hormone receptor antagonists, comprising administering to the patient an effective amount of the described composition. The diseases or conditions may include cancers that express high levels of the growth hormone receptor; high levels of the prolactin receptor; or high levels of both the growth hormone receptor and the prolactin receptor. The cancers may include breast cancer, central nervous system cancer, melanoma, non-small cell lung cancer, ovarian cancer, prostate cancer, and renal cancer. This implementation may also include a variant wherein the following amino acids mutations have been made: H18D, H21N, R167N, K168A, D171S, K172R, E174S, and I179T, and wherein these mutations are operative to prevent binding to a prolactin receptor. This variant may be used in a method for treating acromegaly, comprising administering to the patient an effective amount of the disclosed composition.

Still another implementation provides a third growth hormone receptor antagonist. This growth hormone receptor antagonist comprises human growth hormone receptor antagonist G120K, wherein one amino acid of human growth hormone receptor antagonist G120K has been mutated to cysteine or wherein two amino acids of human growth hormone receptor antagonist G120K have been mutated to cysteine, and wherein the one amino acid mutated to cysteine is T142, and wherein the two amino acids mutated to cysteine are T142 and H151; and a polyethylene glycol molecule conjugated to each substituted cysteine in the human growth hormone receptor antagonist G120K mutant, wherein the polyethylene glycol molecule conjugated to the one amino acid mutated to cysteine is a polydispersed 40 kDa branched polyethylene glycol molecule; and wherein the polyethylene glycol molecules conjugated to the two amino acids mutated to cysteine are two 40 kDa branched polyethylene glycol molecules, two 20 kDa branched polyethylene glycol molecules, two 20 kDa linear polyethylene glycol molecules, or two 4.5 kDa branched polyethylene glycols each containing three carboxylate anions; and wherein the human growth hormone receptor antagonist is encoded by a DNA sequence having at least 95% identity to a DNA molecule selected from the group consisting of SEQ ID NOS: 15 and 23, and wherein the human growth hormone receptor antagonist has an amino acid sequence selected from the group consisting of SEQ ID NO: 16 and 24. The polyethylene glycol molecule may contain a malemide group for conjugation to a free sulfhydryl group. This implementation may also include a method for treating diseases or conditions responsive to human growth hormone receptor antagonists, comprising administering to the patient an effective amount of the described composition. The diseases or conditions may include cancers that express high levels of the growth hormone receptor; high levels of the prolactin receptor; or high levels of both the growth hormone receptor and the prolactin receptor. The cancers may include breast cancer, central nervous system cancer, melanoma, non-small cell lung cancer, ovarian cancer, prostate cancer, and renal cancer. This implementation may also include a variant wherein the following amino acids mutations have been made: H18D, H21N, R167N, K168A, D171S, K172R, E174S, and I179T, and wherein these mutations are operative to prevent binding to a prolactin receptor. This variant may be used in a method for treating acromegaly, comprising administering to the patient an effective amount of the disclosed composition.

It should be appreciated that all combinations of the foregoing concepts and additional concepts discussed in greater detail below (provided such concepts are not mutually inconsistent) are contemplated as being part of the inventive subject matter disclosed herein and may be implemented to achieve the benefits as described herein. Additional features and aspects of the disclosed system, devices, and methods will become apparent to those of ordinary skill in the art upon reading and understanding the following detailed description of the example implementations. As will be appreciated by the skilled artisan, further implementations are possible without departing from the scope and spirit of what is disclosed herein. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more example implementations of the disclosed inventive subject matter and, together with the general description given above and detailed description given below, serve to explain the principles of the disclosed subject matter, and wherein:

FIG. 7A depicts plate 1 of an epithelial cell to mesenchymal cells transition cell transition (EMT) colony formation assay, wherein plate 1 is a control plate;

FIG. 7B depicts plate 2 of an epithelial cell to mesenchymal cells transition cell transition (EMT) colony formation assay, wherein hGH antagonist G120K (A) has been added to plate 2;

FIG. 7C depicts plate 3 of an epithelial cell to mesenchymal cells transition cell transition (EMT) colony formation assay, wherein hGH antagonist T142C-GL2 (D), has been added to plate 3;

FIG. 7D depicts plate 4 of an epithelial cell to mesenchymal cells transition cell transition (EMT) colony formation assay, wherein hGH antagonist H151C-T142C-DPEG®A2(G) has been added to plate 4;

FIG. 7E depicts plate 5 of an epithelial cell to mesenchymal cells transition cell transition (EMT) colony formation assay, wherein plate 5 is a control plate to which hGH has been added;

FIG. 7F depicts plate 6 of an epithelial cell to mesenchymal cells transition cell transition (EMT) colony formation assay, wherein hGH antagonist G120K (A)+hGH has been added to plate 6;

FIG. 7G depicts plate 7 of an epithelial cell to mesenchymal cells transition cell transition (EMT) colony formation assay, wherein hGH antagonist T142C-GL2 (D)+hGH has been added to plate 7; and FIG. 7H depicts plate 8 of an epithelial cell to mesenchymal cells transition cell transition (EMT) colony formation assay, wherein hGH antagonist H151C-T142C-DPEG®A2(G)+hGH has been added to plate 8.

DETAILED DESCRIPTION

Figure 1A:
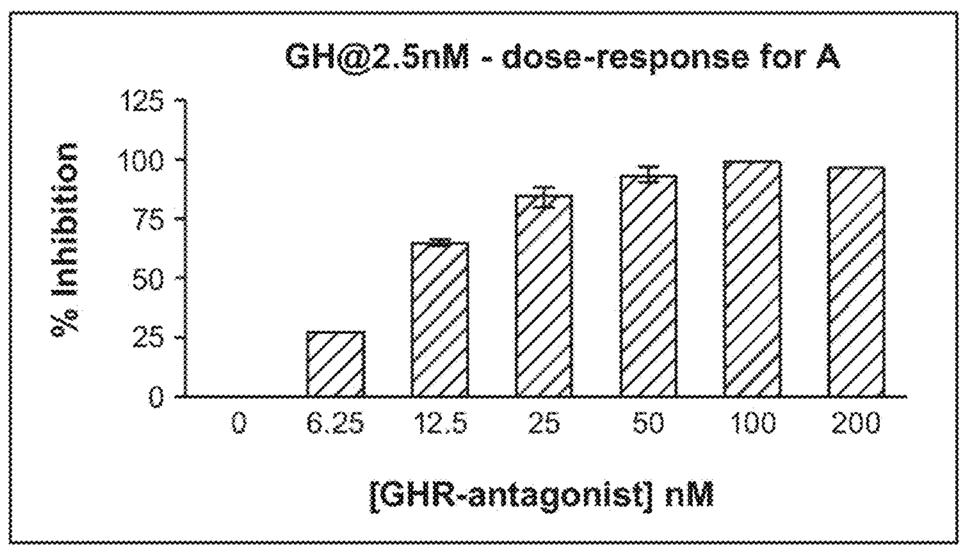
FIG. 1A is a bar chart depicting inhibition of hGH stimulation of Stat5 phosphorylation by non-pegylated hGH antagonist G120K (A), wherein antagonist concentration is represented on the x-axis and wherein percent inhibition is represented on the y-axis.

Example implementations are now described with reference to the Figures. Reference numerals are used throughout the detailed description to refer to the various elements and structures. Although the following detailed description contains many specifics for the purposes of illustration, a person of ordinary skill in the art will appreciate that many variations and alterations to the following details are within the scope of the disclosed inventive subject matter. Accordingly, the following implementations are set forth without any loss of generality to, and without imposing limitations upon, the claimed subject matter.

The present invention provides novel human growth hormone (hGH) antagonists for use primarily as therapeutics, particularly cancer therapeutics. U.S. patent application Ser. No. 16/216,230, (published as US2019/0099497) which is incorporated herein by reference in its entirety for all purposes, discloses the preparation of hGH antagonist molecules that are pegylated in predetermined positions. The hGH antagonists of this invention are typically made by mutating one or more selected amino acids of hGH G120K, a known hGH antagonist, to cysteines and then conjugating the cysteines to chemically activated polyethylene glycol molecules. The positions of the various substituted cysteines were selected for minimal loss in hGH receptor binding activity after conjugation with polyethylene glycol. The size and the number of PEGs added were selected to prevent filtration of these molecules in the kidneys, thereby prolonging in vivo half-lives.

Two important variables in the preparation of the disclosed hGH antagonists include: (i) the amino acid position used for PEG attachment; and (ii) the size and type of the conjugated PEG. Initial research with similar compositions was done using random attachment of relatively small PEGs (e.g., about 5 kDa) to multiple lysines on the surfaces of proteins. This procedure successfully increased the in vivo half-lives of the proteins but resulted in large decreases in the affinity of the proteins for their receptors. More recent experimental approaches have added PEG molecules to specific amino acid sites on proteins. Two common methods used for site specific Pegylation are: (i) addition of PEG to the N-terminal amine of proteins by way of low pH reductive amination; and (ii) addition of PEG to the thiol groups of cysteines that are either native to the protein or engineered into specific positions. Other methods include PEG addition to unnatural amino acids; PEG addition to proteins C-termini by way of intein fusion proteins; and PEG addition to accessible glutamines by way of transaminase catalysis.

Two different types or classes of polyethylene glycol (PEG) molecules are utilized with the present invention. The first class of PEGs was prepared by polymerization and is useful for modifying proteins to increase their in vivo half-lives. This type of PEG is by nature polydispersed, meaning that there is a distribution of molecular weight products around the average molecular weight. The PEGs include a 20 kDa linear PEG (Layson Bio, MPEG-MAL-20,000), a 40 kDa branched PEG (NOF, Sunbright GL2-400MA), and a linear 40 kDa PEG (NOF, Sunbright ME-400MA). These PEGS each contain a maleimide group for conjugation to the free sulfhydryl groups of the mutant proteins. The second class of polyethylene glycols are DPEGS® (discrete polyethylene glycols)(Quanta BioDesign). These DPEGS® (discrete polyethylene glycols) are pure single PEG molecules that are prepared using stepwise, organic chemistry so that each DPEGS® (discrete polyethylene glycols) species is a pure single compound with a specific structure and molecular weight. The DPEGS® (discrete polyethylene glycols) used in this invention, which typically contain a maleimide group for coupling to free thiols, may include the following: a tri-branched molecule with a molecular weight of 4473 Daltons and a carboxylate anion at the terminus of each branch (Quanta BioDesign #10451, MAL-DPEG®A); a neutral tri-branched molecule with a molecular weight of 4299 Daltons (Quanta BioDesign #4229, MAL-DPEG® B); a neutral 9-branched molecule with a molecular weight of 8324 (Quanta Biodesign #10484; MAL-DPEG®E); and a neutral 9-branched molecule with a molecular weight of 15,592 (Quanta Biodesign #11487; MAL-DPEG®F).

Certain of these pegylated antagonists were tested with melanoma cells to determine the ability of these molecules to inhibit the activation of the hGH receptor by hGH; to sensitize these cells to chemotherapy treatment; to inhibit basement membrane invasion stimulated by hGH; and to inhibit hGH stimulated colony formation of non-adherent melanoma cells. Table I, below, includes names and abbreviations for specific human growth hormone (hGH) antagonists disclosed herein.

TABLE I

Designations for Mutant hGH Antagonists

| Name | Abbreviation | Letter Designation | SED ID NOS: |
|---|---|---|---|
| hGH-G120K | G120K | A | 3-4 |
| hGH-G120K-T142C-GL2-400MA | T142C-GL2 | D | 15-16 |
| hGH-G120K-H151C-GL2-400MA | H151C-GL2 | — | 17-18 |
| hGH-G120K-N99C-T142C-DPEG ®$A_2$ | N99C-T142C-DPEG ®$A_2$ | G | 21-22 |
| hGH-G120K-H151C-T142C-DPEG ®$A_2$ | H151C-T142C-DPEG ®$A_2$ | — | 23-24 |

All test samples contained the G120K mutation of hGH, which converts the hormone to a hormone antagonist. Single mutants containing either the T142C or H151C mutation were conjugated through their added cysteine to a 40 kDa two branched polyethylene glycol (GL2-400MA). Double mutants containing either N99C and T142C or H151C and T142C had both cysteine positions conjugated to a 4.5 kDa tri-branched polyethylene glycol with a carboxyl group at the end of each branch.

Relative Affinity for the hGH Receptor Determined by Competition ELISA Assays

The amino acid positions of G120K that were mutated to cysteine and subsequently pegylated were selected on the basis of amino acid accessibility and structural energy criteria (see U.S. patent application Ser. No. 16/216,230). Despite the fact that the pegylated mutants were all selected by the same method, there are differences in the affinities of the pegylated mutants for the hGH receptor (see U.S. patent application Ser. No. 16/216,230; Table 2, which is also reproduced herein as TABLE 2). The relative binding affinities of the single mutants substituted with DPEG®A varied between 20% and 100% of the affinity of hGH.

Within a series of similar DPEG®s, the size of the PEG substituent makes a difference in receptor binding affinity (see TABLE 2, below), with the larger DPEG®E (8.3 kDa) and DPEG®F (15.6 kDa) binding more poorly than the smaller DPEG®A (4.5 kDa) or DPEG®B (4.3 kDa). However, PEG size is not the only predictor of hGH receptor binding affinity; the structure of the PEG is also important. Mutants substituted at positions N99C, T142C, and H151C with the 15.6 kDa DPEG®F, which contains nine branches, bind to the hGH receptor with relative affinities of 4%, 20%, and 4% respectively. In contrast, the same three mutants conjugated to a 40 kDa PEG (GL2-MA; 2 branches) all bound to the receptor with 50% of the affinity of hGH.

TABLE 2

Receptor Binding Activity of hGH 120K Mutants[1]

| hGH Mutant All Mutants Contain the G120K Mutation | Percent Receptor Binding Activities Relative to that of hGH Determined from the Concentration of Each Sample that Yields 50% Inhibition ($I_{50}$) | | | |
|---|---|---|---|---|
| DPEG ® Substitution | dPEGA[2] | dPEGB[2] | dPEGE[2] | dPEGF[2] |
| G120K-T3C-DPEG ®X | 70 | 70 | NT | NT |
| G120K-E39C-DPEG ®X | 20 | NT | NT | NT |
| G120K-P48C-DPEG ®X | 20 | NT | NT | NT |
| G120K-Q69C-DPEG ®X | 20 | NT | NT | NT |
| G120K-N99C-DPEG ®X | 90 | 70 | 40 | 4 |
| G120K-T142C-DPEG ®X | 50 | 90 | 50 | 20 |
| G120K-H151C-DPEG ®X | 100 | 60 | 40 | 4 |
| G120K-N99C-DPEG ®X-H151C-DPEG ®X | 20 | 40 | 20 | —[3] |
| G120K-T142C-DPEG ®X-N99C-DPEG ®X | 50 | 80 | 30 | —[3] |
| G120K-T142C-DPEG ®X-H151C-DPEG ®X | 50 | 40 | 10 | —[3] |

[1]The receptor binding activities were determined using a competitive ELISA where the recombinant receptor was bound to a plate and the concentration of each sample needed to inhibit the binding of biotin-hGH to the coated plate by 50% (I50) was determined. The Table entries show the $I_{50}$s relative to that of hGH, which is defined as 100%, and are rounded to a single significant figure. Only a single competitive ELISA was run for most of the mutants and the estimated relative standard deviation is 25%. Entries marked NT were not tested in this assay.

[2]DPEG ®A is a tri-branched molecule with a molecular weight of 4473 Daltons and a carboxylate anion at the terminus of each branch; DPEG ®B is a neutral tri-branched molecule with a molecular weight of 4299 Daltons, DPEG ®E is a neutral 9-branched molecule with a molecular weight of 8324; and DPEG ®F is a neutral 9-branched molecule with a molecular weight of 15,592.

[3]These reactions did not proceed to the double PEGylated product.

Determination of the Abilities of Pegylated hGH Antagonists to Inhibit the Stimulation of Stat5 Phosphorylation by hGH Four pegylated mutant antagonists were selected and tested for their abilities to inhibit the hGH stimulation of Stat5 phosphorylation in three human cancer cell lines at a single antagonist concentration. As illustrated in TABLE 3, below, these mutants were all effective antagonists at 50 nM, with the exception of H151C-GL2 with the IM9 cell line.

TABLE 3

Inhibition of hGH Stimulation of Stat5 Phosphorylation in Different Cell Lines[1]

| | CELL LINES[2] | | |
|---|---|---|---|
| TARGET | IM9 % Inhibition | PANC1 % Inhibition | MALME3M % Inhibition |
| T142C-GL2 | 70 | 80 | 60 |
| H151C-GL2 | 1 | 50 | 60 |
| N99C-T142C-PEG ®$A_2$ | 70 | 100 | 90 |
| H151C-T142C-DPEG ®$A_2$ | 70 | 90 | 90 |

[1]Stat5 phosphorylation was measure by ELISA after the cells were incubated with 2.5 nM hGH + 50 nM of the antagonist sample.

Figure 1B:
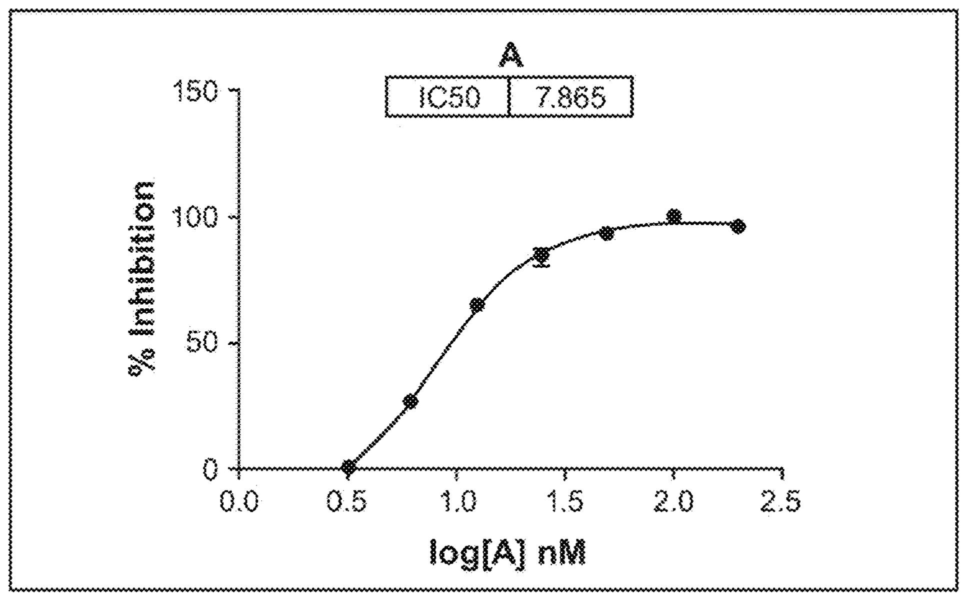
FIG. 1B is a graph depicting inhibition of hGH stimulation of Stat5 phosphorylation by non-pegylated hGH antagonist G120K (A), wherein antagonist concentration is represented on the x-axis and wherein percent inhibition is represented on the y-axis.
Figure 1C:
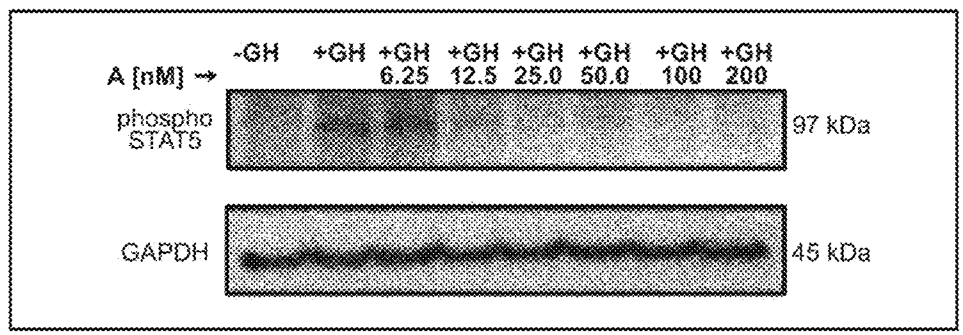
FIG. 1C is a western blot analysis depicting inhibition of hGH stimulation of Stat5 phosphorylation by non-pegylated hGH antagonist G120K (A) at increasing nM concentrations of hGH antagonist (2.5 nM hGH)
Figure 2A:
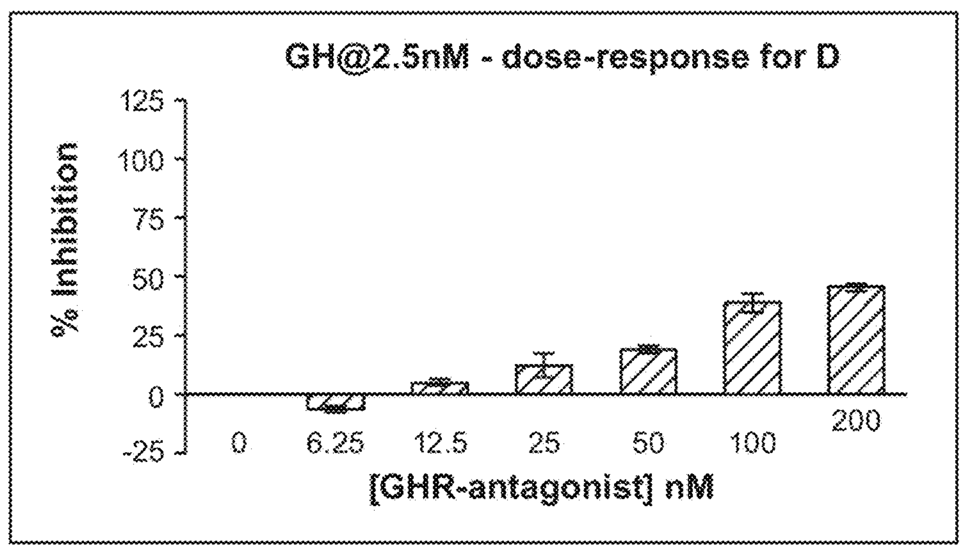
FIG. 2A is a bar chart depicting inhibition of hGH stimulation of Stat5 phosphorylation by pegylated hGH antagonist T142C-GL2 (D), wherein antagonist concentration is represented on the x-axis and wherein percent inhibition is represented on the y-axis.
Figure 2B:
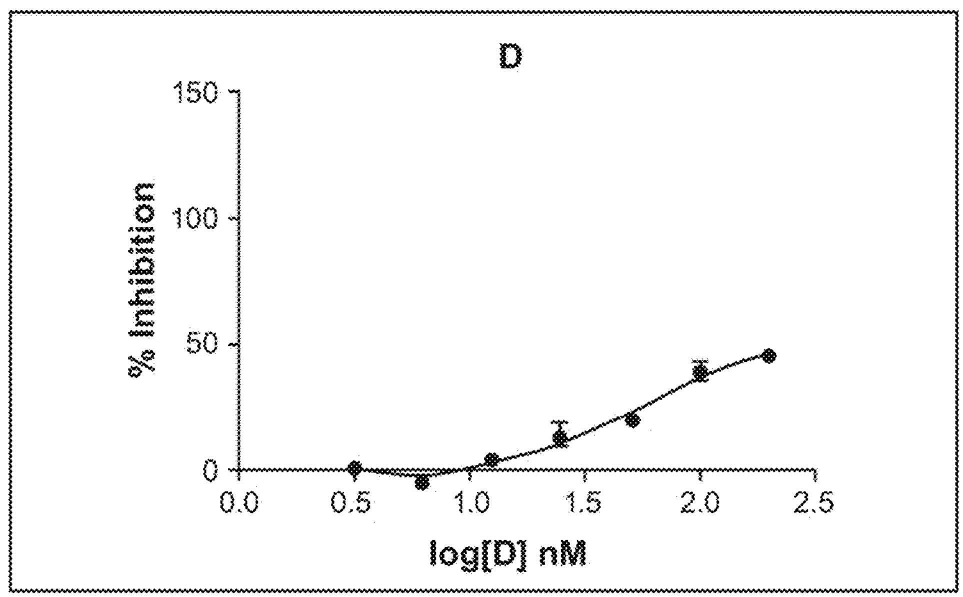
FIG. 2B is a graph depicting inhibition of hGH stimulation of Stat5 phosphorylation by pegylated hGH antagonist G120K (D), wherein antagonist concentration is represented on the x-axis and wherein percent inhibition is represented on the y-axis.
Figure 2C:
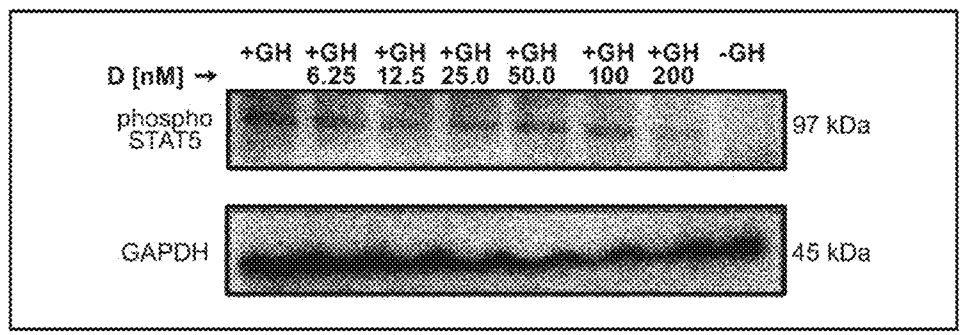
FIG. 2C is a western blot analysis depicting inhibition of hGH stimulation of Stat5 phosphorylation by pegylated hGH antagonist G120K (D) at increasing nM concentrations of hGH antagonist (2.5 nM hGH)
Figure 3A:
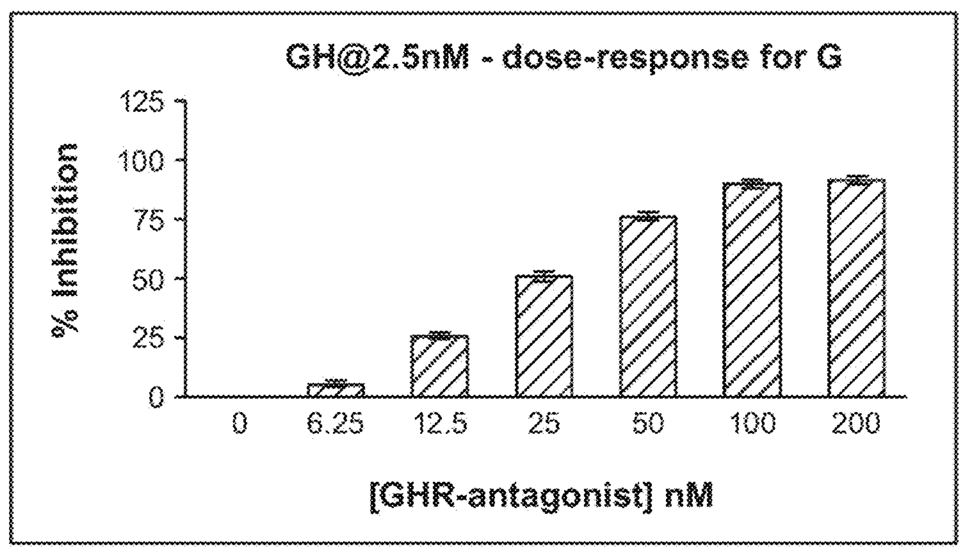
FIG. 3A is a bar chart depicting inhibition of hGH stimulation of Stat5 phosphorylation by pegylated hGH antagonist H151C-T142C-DPEG®A2 (G), wherein antagonist concentration is represented on the x-axis and wherein percent inhibition is represented on the y-axis.
Figure 3B:
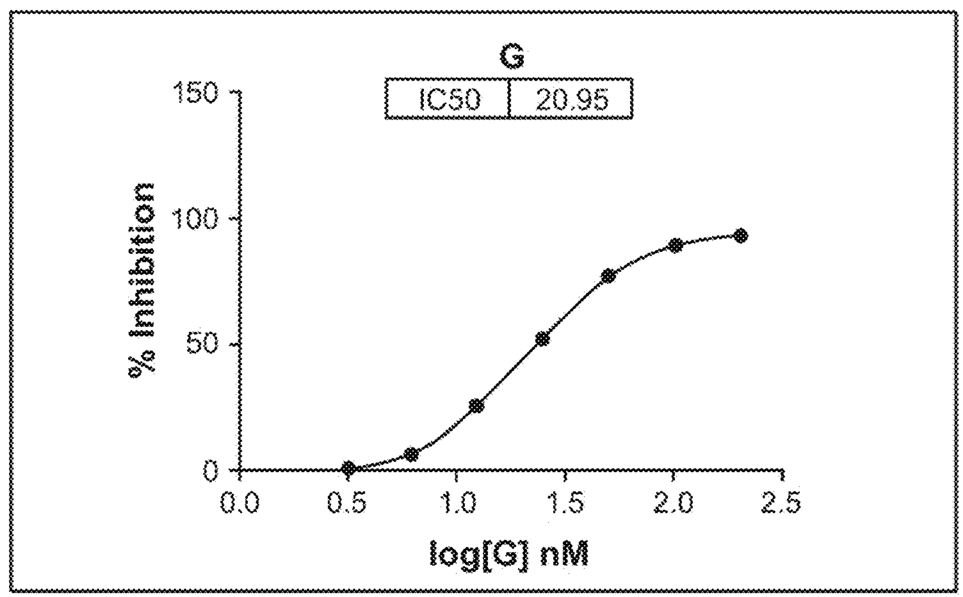
FIG. 3B is a graph depicting inhibition of hGH stimulation of Stat5 phosphorylation by pegylated hGH antagonist H151C-T142C-DPEG®A2 (G), wherein antagonist concentration is represented on the x-axis and wherein percent inhibition is represented on the y-axis.
Figure 3C:
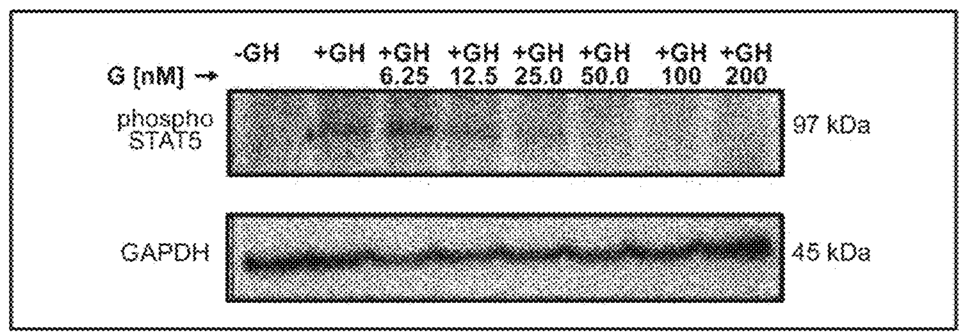
FIG. 3C is a western blot analysis depicting inhibition of hGH stimulation of Stat5 phosphorylation by pegylated hGH antagonist H151C-T142C-DPEG®A2 (G) at increasing nM concentrations of hGH antagonist (2.5 nM hGH)

[2]The cell lines used are as follows
IM9; human lymphoblast, transformed
PANC1; human pancreatic adenocarcinoma
MALME3M; melanoma Pegylated mutant hGH antagonists T142-GL2 (D) and H151C-T142C-DPEG®$A_2$ (G) were selected for further testing with melanoma cells using non-pegylated mutant G120K (A) as a control. FIGS. 1A-1C; 2A-2C; and 3A-3C illustrate effective inhibition of Stat5 phosphorylation stimulation by the selected compounds at different concentrations. FIGS. 1A-1B; 2A-2B; and 3A-3B provide data generated by ELISA demonstrating that fifty percent inhibition requires a 2.7× higher concentration of H151C-T142C-DPEG®$A_2$ (G) than the required concentration of G120K (A). Therefore, H151C-T142C-DPEG®$A_2$ (G) has about 40% of the inhibitory power of G120K. FIGS. 1C; 2C; and 3C depict western blot data that is consistent with the ELISA results shown in the Figures. At the highest concentration tested (200 nM), T142C-GL2 (D) inhibited hGH stimulation of Stat5 phosphorylation by 50% as determined by ELISA (FIGS. 2A-2B). In contrast, H151C-T142C-DPEG®$A_2$ (G) at 100 nm completely inhibited hGH stimulation (FIGS. 3A-3B). These results indicate that the relative abilities of pegylated mutant hGH antagonists to bind to the soluble hGH receptor are not predictive of the abilities of these antagonists to inhibit hGH stimulation of Stat5 phosphorylation in different cancer cell lines.

Figure 4A:
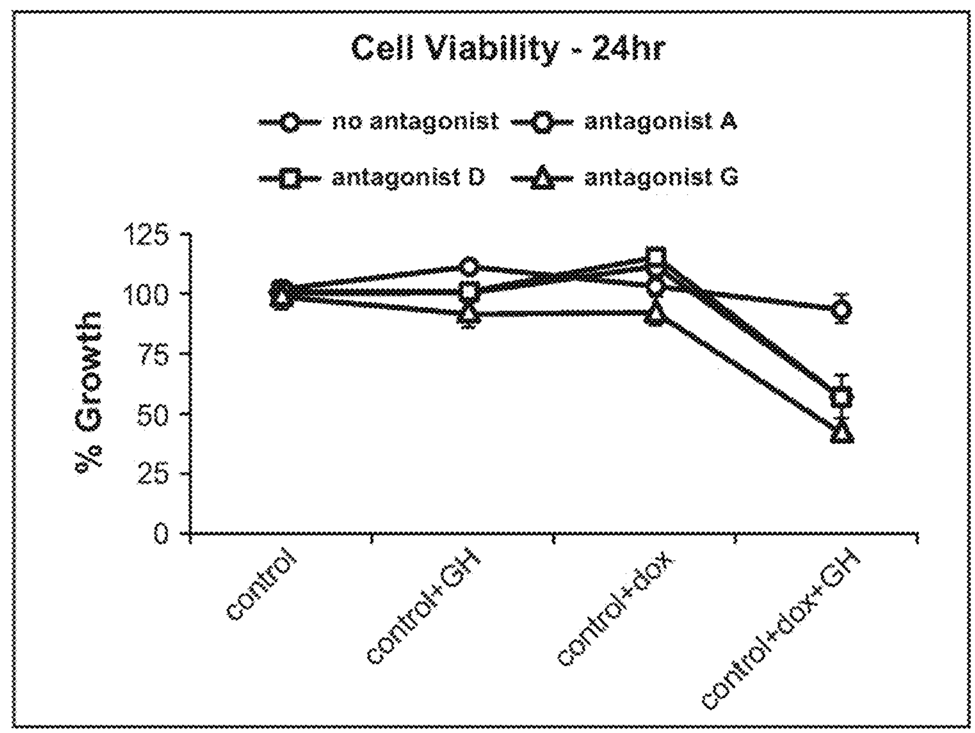
FIG. 4A is a graph depicting cell viability after 24 hours in the presence of no hGH antagonist, hGH antagonist G120K (A), hGH antagonist T142C-GL2 (D), and hGH antagonist H151C-T142C-DPEG®A2 (G), wherein sample type is represented on the x-axis (control, control plus hGH, control plus doxorubicin, control plus doxorubicin plus hGH), and wherein percent growth is represented on the y-axis.
Figure 4B:
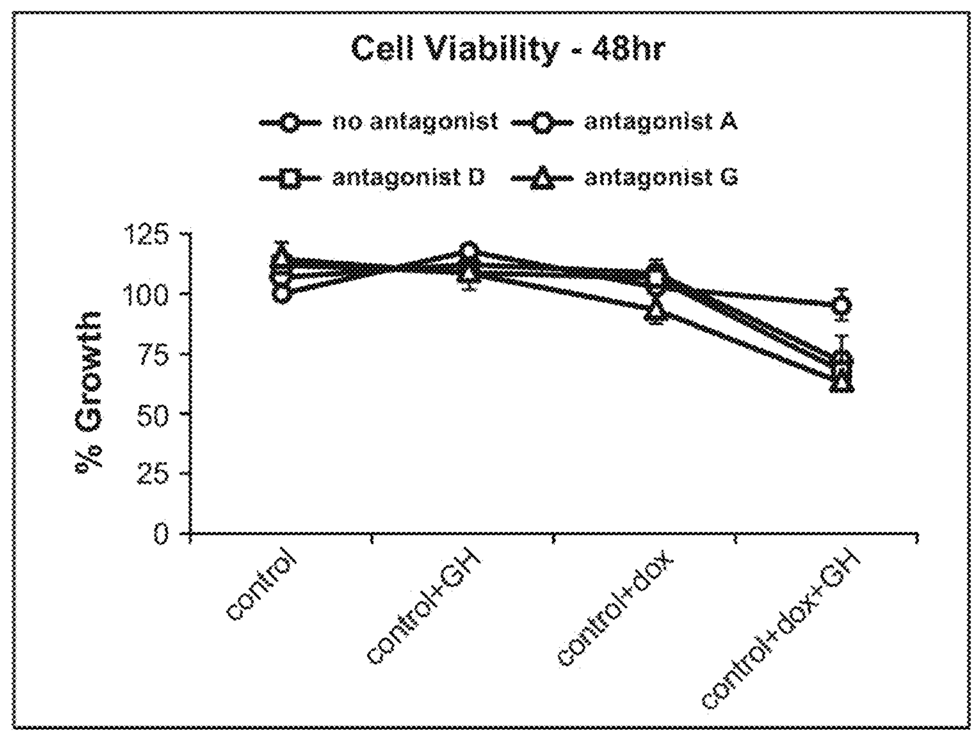
FIG. 4B is a graph depicting cell viability after 48 hours in the presence of no hGH antagonist, hGH antagonist G120K (A), hGH antagonist T142C-GL2 (D), and hGH antagonist H151C-T142C-DPEG®2 (G), wherein sample type is represented on the x-axis (control, control plus hGH, control plus doxorubicin, control plus doxorubicin plus hGH), and wherein percent growth is represented on the y-axis.
Figure 4C:
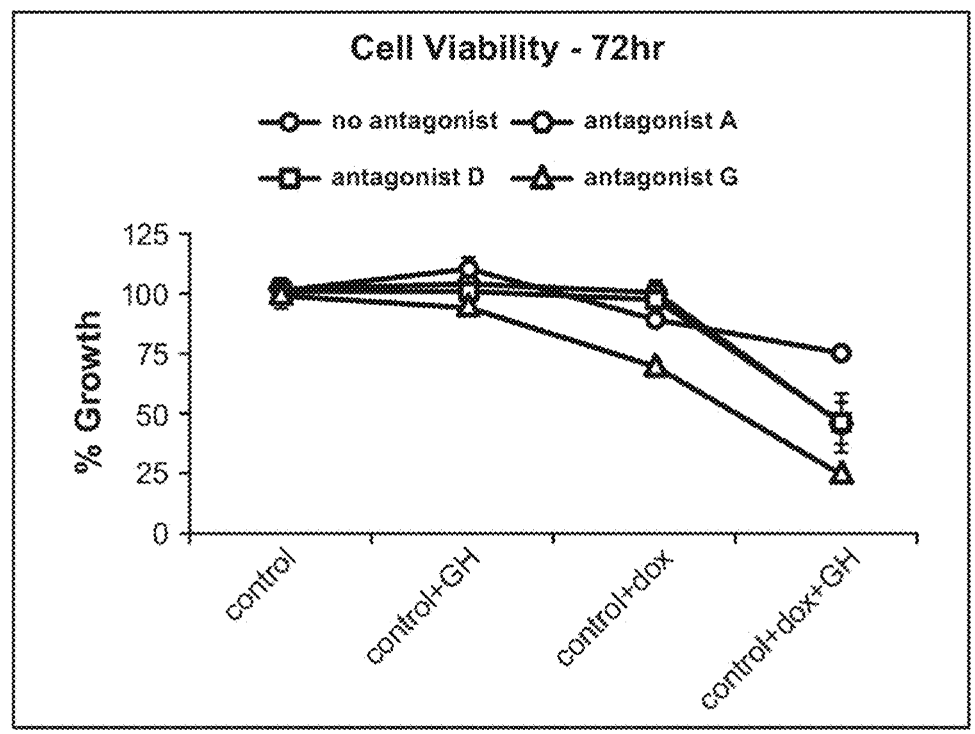
FIG. 4C is a graph depicting cell viability after 72 hours in the presence of no hGH antagonist, hGH antagonist G120K (A), hGH antagonist T142C-GL2 (D), and antagonist H151C-T142C-DPEG® (G), wherein sample type is represented on the x-axis (control, control plus hGH, control plus doxorubicin, control plus doxorubicin plus hGH), and wherein percent growth is represented on the y-axis.
Figure 4D:
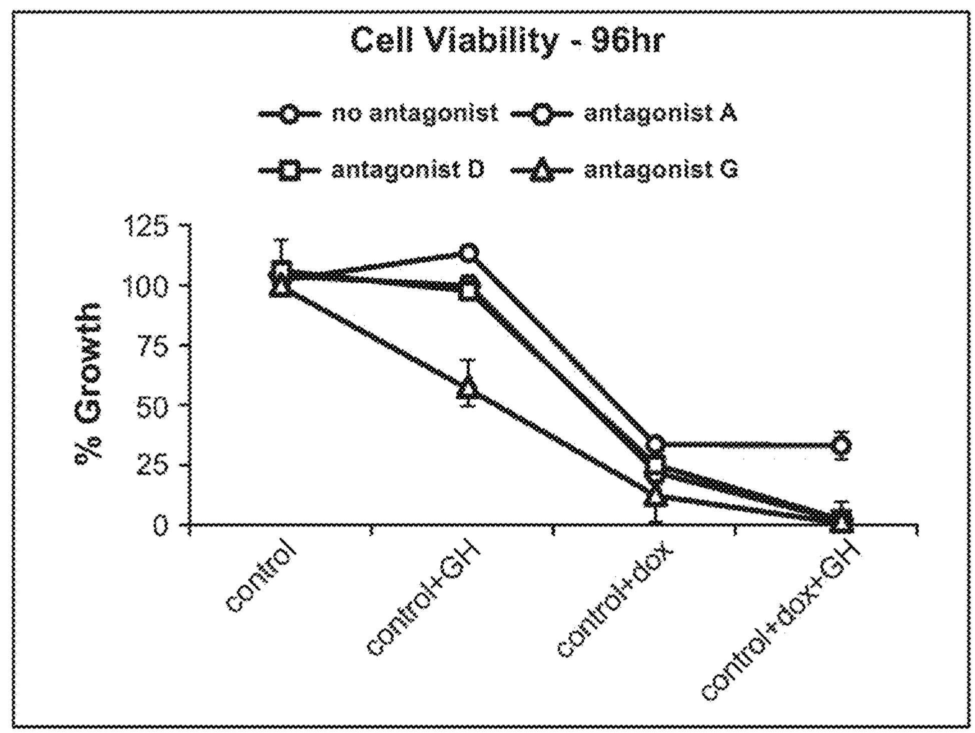
FIG. 4D is a graph depicting cell viability after 96 hours in the presence of no hGH antagonist, hGH antagonist G120K (A), hGH antagonist T142C-GL2 (D), and hGH antagonist H151C-T142C-DPEG®A2 (G), wherein sample type is represented on the x-axis (control, control plus hGH, control plus doxorubicin, control plus doxorubicin plus hGH), and wherein percent growth is represented on the y-axis.

Behavior of Pegylated hGH Antagonists in In Vitro Assays that Correlate with Anti-Cancer Activity Cell Viability Melanoma cells were incubated with pegylated mutant hGH antagonists T142-GL2 (D) and H151C-T142C-DPEG®$A_2$(G) with non-pegylated G120K mutant (A) as a control in the presence of and in the absence of hGH and the chemotherapy drug doxorubicin. As shown in FIGS. 4A-4D, cell viabilities after 24 hours, 48 hours, 72 hours, and 96 hours were determined. Growth hormone has been found to enhance the ability of cells to export chemotherapy drugs and hGH antagonists are predicted to block this enhancement [7]. Accordingly, the pegylated mutant hGH antagonists disclosed herein were expected to decrease the viability of cells treated with growth hormone. In cells treated with growth hormone, H151C-T142C-DPEG®$A_2$ (G) significantly reduced cell viability after 96 hours (FIG. 4D). No difference in viability was observed with the antagonists G120K (A) and T142C-GL2 (D). In cells treated with doxorubicin, H151C-T142C-DPEG® A2 (G) significantly decreased cell viability after 72 hours (FIG. 4C). Again, G120K (A) and T142C-GL2 (D) had no significant effect. In cells treated with hGH plus doxorubicin, G120K (A), T142C-GL2 (D), and H151C-T142C-DPEG®$A_2$(G) all significantly decreased cell viability after only 24 hours (FIG. 4A).

Basement Membrane Migration

Figure 5:
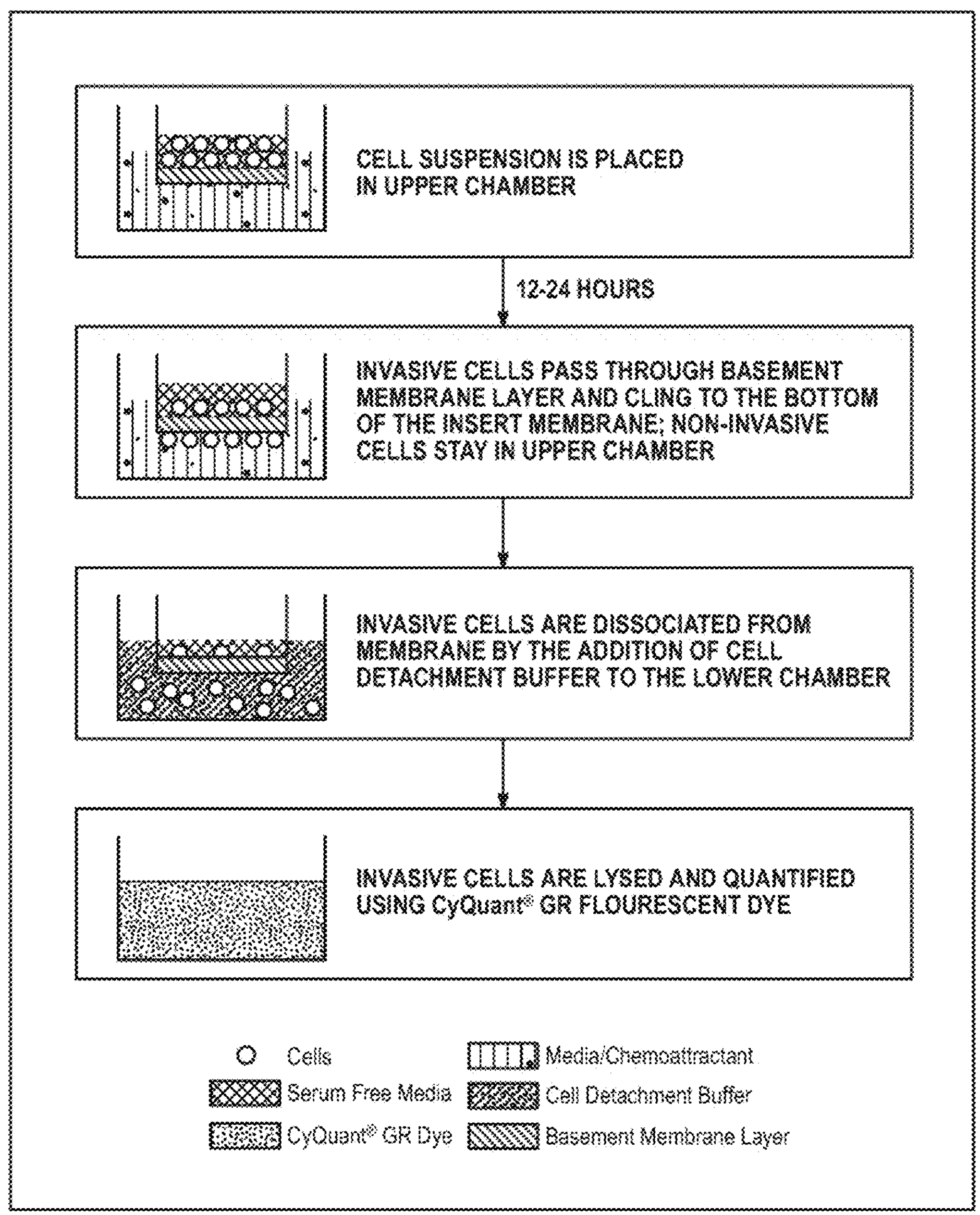
FIG. 5 is a flow chart depicting a general method for measuring basement membrane migration of cells such as, for example, cancer cells.

A known characteristic of cancer cells is their ability to migrate through basement membranes. This migration may be inhibited by chemotherapeutic agents such as doxorubicin. A general method for measuring basement membrane migration of cells, such as cancer cells, is shown in FIG. 5. In a first step of the method shown in FIG. 5, a cell suspension in serum free media is placed in an upper chamber, the bottom portion of which includes a basement membrane layer. The upper chamber is placed in a lower chamber that includes media containing a chemoattractant. In a second step of the method shown in FIG. 5, after a period of 12-14 hours invasive cells pass through the basement membrane layer and cling to the bottom of the membrane and non-invasive cells remain in the upper chamber. In a third step of the method shown in FIG. 5 invasive cells are disassociated from the membrane by the addition of cell detachment buffer to the lower chamber. Finally, in a fourth step of the method shown in FIG. 5, invasive cells are lysed and quantified using CyQuant® GR Fluorescent Dye.

Figure 6A:
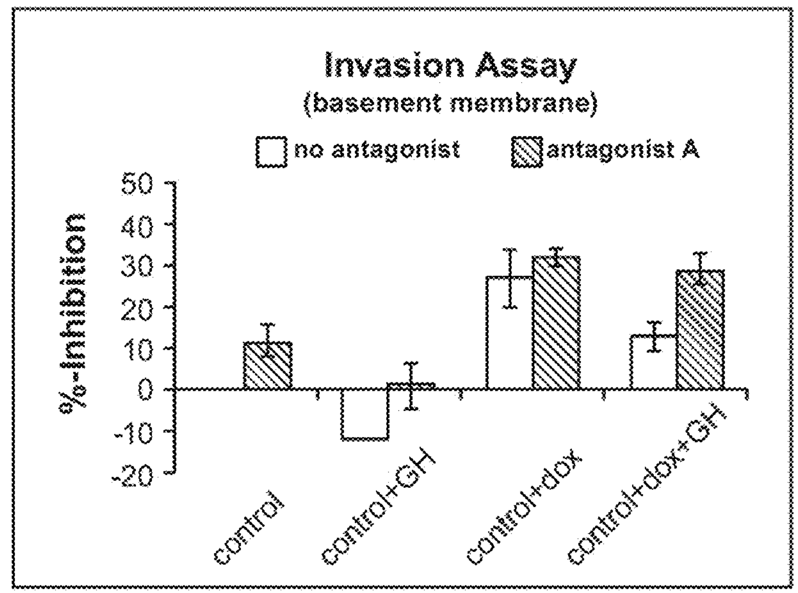
FIG. 6A is a bar chart depicting the results of a basement membrane inhibition (invasion) assay using no hGH antagonist and hGH antagonist G120K (A), wherein sample type is represented on the x-axis (control, control plus hGH, control plus doxorubicin, control plus doxorubicin plus hGH), and wherein percent inhibition is represented on the y-axis.
Figure 6B:
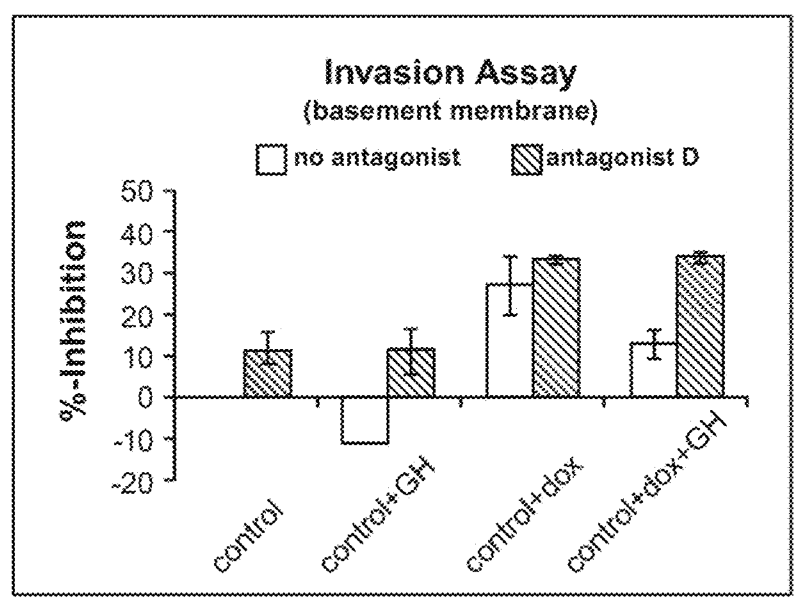
FIG. 6B is a bar chart depicting the results of a basement membrane inhibition (invasion) assay using no hGH antagonist and hGH antagonist T142C-GL2 (D), wherein sample type is represented on the x-axis (control, control plus hGH, control plus doxorubicin, control plus doxorubicin plus hGH), and wherein percent inhibition is represented on the y-axis.
Figure 6C:
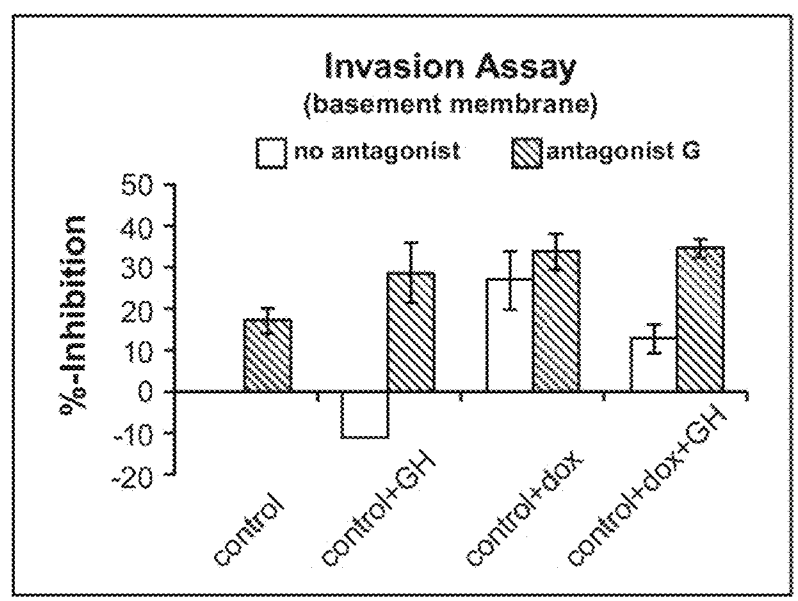
FIG. 6C is a bar chart depicting the results of a basement membrane inhibition (invasion) assay using no hGH antagonist and antagonist H151C-T142C-DPEG®A2 (G), wherein sample type is represented on the x-axis (control, control plus hGH, control plus doxorubicin, control plus doxorubicin plus hGH), and wherein percent inhibition is represented on the y-axis.

Results of a basement membrane inhibition assay with melanoma cells and the hGH antagonists G120K (A), T142C-GL2 (D), and H151C-T142C-DPEG®A2(G) are shown in FIGS. 6A-6C. The results for G120K (A) and for the pegylated inhibitors T142C-GL (D) and H151C-T142C-DPEG®A2 (G) are similar. The addition of doxorubicin to melanoma cells inhibits the basement membrane migration with and without the addition of the hGH antagonists. The addition of hGH to cells treated with doxorubicin without the antagonists significantly reduces this inhibition. Essentially, hGH counteracts the effects of doxorubicin, most likely by stimulating the cell to pump out the doxorubicin and allows the melanoma cells to show increased migration. When cells are treated with the antagonists plus doxorubicin plus hGH, the antagonists reverse the effect of hGH and the inhibition of basement membrane migration reverts to the higher value found in the absence of hGH.

Colony Formation of Non Adherent Melanoma Cells

The transition of epithelial cells to mesenchymal cells is associated with cancer metathesis. Non-adherence is a key marker of the epithelial-mesenchymal transition. Adherent melanoma cells were treated with either hGH or hGH plus hGH antagonist and non-adherent cells were assayed for their ability to form colonies (FIGS. 7A-7H). In the absence of hGH (Plates 1-4, shown in FIGS. 7A-7D), the number of colonies was approximately the same with and without G120K (A), T142C-GL2 (D), and H151C-T142C-DPEG®$A_2$ (G). The addition of hGH to the control (Plate 5, shown in FIG. 7E) resulted in a clear increase in colony formation. The addition of G120K (A) plus hGH also resulted in increased colony formation (Plate 6, shown in FIG. 7F). However, the colony formation was clearly reduced when either hGH antagonist T142C-GL2 (D) or H151C-T142C-DPEG®$A_2$ (G) were added to hGH. Thus, the two pegylated antagonists reverse the ability of growth hormone to enhance the viability of non-adherent cells.

Binding to the Prolactin Receptor

Both human prolactin and hGH bind to and activate the prolactin receptor. The activation of this receptor has been implicated in breast cancer pathogenesis and behavior [8]. Binding of pegylated hGH antagonists T142C-GL2, H151C-GL2, N99C-T142C-DPEG®A2, and H151C-T142C-DPEG®$A_2$ to the soluble prolactin receptor in a competitive ELISA assay determined that hGH and the pegylated antagonists listed in TABLE 2 (see also, U.S. patent application Ser. No. 16/216,230, Table 2) bind to the prolactin receptor with the relative binding affinities shown in TABLE 4, below.

TABLE 4

Relative Binding Affinities of Pegylated hGH Antagonists for the Prolactin Receptor Protein

| Compound | Abbreviation |
|---|---|
| hGH | 100% |
| T142C-GL2 | 50% |
| H151C-GL2 | 40% |
| N99C-T142C-DPEG ®$A_2$ | 60% |
| H151C-T142C-DPEG ®$A_2$ | 70% |

These antagonists are therefore expected to inhibit any facilitation of cancer cell growth mediated by activation of the prolactin receptor by either hGH or prolactin. This is in contrast to the current therapeutic growth hormone antagonist (SOMAVERT®) (pegvisomant), which does not bind to the prolactin receptor [8]-[9].

Growth Hormone Antagonists as Potential Acromegaly Therapeutics

The pegylated growth hormone antagonist SOMAVERT® (pegvisomant) has been approved for treatment of acromegaly. This molecule, which comprises hGH-G120K and eight (8) additional mutations, has four to six 5 kDa linear PEG molecules attached to random lysine residues. The eight additional mutations increase drug affinity for the soluble growth hormone receptor and remove its affinity for the prolactin receptor. SOMAVERT® (pegvisomant) is an effective treatment for acromegaly even though its randomly conjugated PEG molecules reduce its affinity for the hGHR by about 20-fold [10]. The hGH antagonists disclosed herein, with one or two specifically substituted PEGS, only reduce the receptor affinity about 2-fold, making these compounds potentially more effective as acromegaly treatment. However, in order to prepare an acromegaly treatment, the disclosed pegylated antagonists will be modified to prevent off-target prolactin receptor binding, requiring the following mutations: H18D, H21N, R167N, K168A, D171S, K172R, E174S, and I179T [11].

As indicated by the disclosure above, the compositions of the present invention provide novel human growth hormone receptor antagonists that are useful in therapeutic applications. For reference purposes, SEQ ID NO: 1 provides the DNA sequence for human growth hormone WThGH and SEQ ID NO: 2 and provides the amino acid sequence for human growth hormone WThGH (mature form), referred to herein as hGH. Human growth hormone receptor antagonist hGH-G120K, referred to herein as G120K, is the parent receptor antagonist for the compositions of the present invention, and for reference purposes, SEQ ID NO: 3 provides the DNA sequence for human growth hormone receptor antagonist G120K and SEQ ID NO: 4 provides the amino acid sequence for human growth hormone receptor antagonist G120K (mature form). The single letter amino acid abbreviations used herein follow the IUPAC format.

A first example human growth hormone antagonist disclosed herein includes human growth hormone antagonist G120K, wherein amino acid T3 has been mutated to cysteine, and wherein a polyethylene glycol molecule has been conjugated to the cysteine mutation. SEQ ID NO: 5 provides the DNA sequence for human growth hormone antagonist G120K-T3C and SEQ ID NO: 6 provides the amino acid for sequence human growth hormone antagonist G120K-T3C.

A second example human growth hormone antagonist disclosed herein includes human growth hormone antagonist G120K, wherein amino acid E39 has been mutated to cysteine, and wherein a polyethylene glycol molecule has been conjugated to the cysteine mutation. SEQ ID NO: 7 provides the DNA sequence for human growth hormone antagonist G120K-E39C and SEQ ID NO: 8 provides the amino acid sequence for human growth hormone antagonist G120K-E39C.

A third example human growth hormone antagonist disclosed herein includes human growth hormone antagonist G120K, wherein amino acid P48 has been mutated to cysteine, and wherein a polyethylene glycol molecule has been conjugated to the cysteine mutation. SEQ ID NO: 9 provides the DNA sequence for human growth hormone antagonist G120K-P48C and SEQ ID NO: 10 provides the amino acid sequence for human growth hormone antagonist G120K-P48C.

A fourth example human growth hormone antagonist disclosed herein includes human growth hormone antagonist G120K, wherein amino acid Q69 has been mutated to cysteine, and wherein a polyethylene glycol molecule has been conjugated to the cysteine mutation. SEQ ID NO: 11 provides the DNA sequence for human growth hormone antagonist G120K-Q69C and SEQ ID NO: 12 provides the amino acid sequence for human growth hormone antagonist G120K-Q69C.

A fifth example human growth hormone antagonist disclosed herein includes human growth hormone antagonist G120K, wherein amino acid N99 has been mutated to cysteine, and wherein a polyethylene glycol molecule has been conjugated to the cysteine mutation. SEQ ID NO: 13 provides the DNA sequence for human growth hormone antagonist G120K-N99C and SEQ ID NO: 14 provides the amino acid sequence for human growth hormone antagonist G120K-N99C.

A sixth example human growth hormone antagonist disclosed herein includes human growth hormone antagonist G120K, wherein amino acid T142 has been mutated to cysteine, and wherein a polyethylene glycol molecule has been conjugated to the cysteine mutation. SEQ ID NO: 15 provides the DNA sequence for human growth hormone antagonist G120K-T142C-GL2-400MA, referred to herein as T142C-GL2, and SEQ ID NO: 16 provides the amino acid sequence for human growth hormone antagonist G120K-T142C-GL2-400MA, referred to herein as T142C-GL2.

A seventh example human growth hormone antagonist disclosed herein includes human growth hormone antagonist G120K, wherein amino acid H151 has been mutated to cysteine, and wherein a polyethylene glycol molecule has been conjugated to the cysteine mutation. SEQ ID NO: 17 provides the DNA sequence for human growth hormone antagonist G120K-H151C-GL2-400MA, referred to herein as H151C-GL2, and SEQ ID NO: 18 provides the amino acid sequence for human growth hormone antagonist G120K-H151C-GL2-400MA, referred to herein as H151C-GL2.

An eighth example human growth hormone antagonist disclosed herein includes human growth hormone antagonist G120K, wherein amino acids N99 and H151 have been mutated to cysteine, and wherein a polyethylene glycol molecule has been conjugated to each cysteine mutation. SEQ ID NO: 19 provides the DNA sequence for human growth hormone antagonist G120K-N99C-H151C-DPEG®$A_2$ and SEQ ID NO: 20 provides the amino acid sequence for human growth hormone antagonist G120K-N99C-H151C-DPEG®A2.

A ninth example human growth hormone antagonist disclosed herein includes human growth hormone antagonist G120K, wherein amino acids T142 and N99 have been mutated to cysteine, and wherein a polyethylene glycol molecule has been conjugated to each cysteine mutation. SEQ ID NO: 21 provides the DNA sequence for human growth hormone antagonist G120K-N99C-T142-DPEG®A2, referred to herein as N99C-T142C-DPEG®$A_2$ and SEQ ID NO: 22 provides the amino acid sequence for human growth hormone antagonist G120K-N99C-T142-DPEG®A2, referred to herein as N99C-T142C-DPEG®A2.

A tenth example human growth hormone antagonist disclosed herein includes human growth hormone antagonist G120K, wherein amino acids T142 and H151 have been mutated to cysteine, and wherein a polyethylene glycol molecule has been conjugated to each cysteine mutation. SEQ ID NO: 23 provides the DNA sequence for human growth hormone antagonist G120K-H151C-T142C-DPEG®$A_2$, referred to herein as H151C-T142C-DPEG®A2 and SEQ ID NO: 24 provides the amino acid sequence for human growth hormone antagonist G120K-H151C-T142C-DPEG®A2, referred to herein as H151C-T142C-DPEG®A2.

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated references and similar materials differs from or contradicts this application, including but not limited to defined terms, term usage, described techniques, or the like, this application controls.

As previously stated and as used herein, the singular forms "a," "an," and "the," refer to both the singular as well as plural, unless the context clearly indicates otherwise. The term "comprising" as used herein is synonymous with "including," "containing," or "characterized by," and is inclusive or open-ended and does not exclude additional, unrecited elements or method steps. Although many methods and materials similar or equivalent to those described herein can be used, particular suitable methods and materials are described herein. Unless context indicates otherwise, the recitations of numerical ranges by endpoints include all numbers subsumed within that range. Furthermore, references to "one implementation" are not intended to be interpreted as excluding the existence of additional implementations that also incorporate the recited features. Moreover, unless explicitly stated to the contrary, implementations "comprising" or "having" an element or a plurality of elements having a particular property may include additional elements whether or not they have that property.

The terms "substantially" and "about" used throughout this specification are used to describe and account for small fluctuations, such as due to variations in processing. For example, these terms can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%, and/or 0%.

Underlined and/or italicized headings and subheadings are used for convenience only, do not limit the disclosed subject matter, and are not referred to in connection with the interpretation of the description of the disclosed subject matter. All structural and functional equivalents to the elements of the various implementations described throughout this disclosure that are known or later come to be known to those of ordinary skill in the art are expressly incorporated herein by reference and intended to be encompassed by the disclosed subject matter. Moreover, nothing disclosed herein is intended to be dedicated to the public regardless of whether such disclosure is explicitly recited in the above description.

There may be many alternate ways to implement the disclosed inventive subject matter. Various functions and elements described herein may be partitioned differently from those shown without departing from the scope of the disclosed inventive subject matter. Generic principles defined herein may be applied to other implementations. Different numbers of a given module or unit may be employed, a different type or types of a given module or unit may be employed, a given module or unit may be added, or a given module or unit may be omitted.

It should be appreciated that all combinations of the foregoing concepts and additional concepts discussed in greater detail herein (provided such concepts are not mutually inconsistent) are contemplated as being part of the disclosed inventive subject matter. In particular, all combinations of claimed subject matter appearing at the end of this disclosure are contemplated as being part of the inventive subject matter disclosed herein. While the disclosed inventive subject matter has been illustrated by the description of example implementations, and while the example implementations have been described in certain detail, there is no intention to restrict or in any way limit the scope of the appended claims to such detail. Additional advantages and modifications will readily appear to those skilled in the art. Therefore, the disclosed inventive subject matter in its broader aspects is not limited to any of the specific details, representative devices and methods, and/or illustrative examples shown and described. Accordingly, departures may be made from such details without departing from the spirit or scope of the general inventive concept.

The following references form part of the specification of the present application and each reference is incorporated by reference herein, in its entirety, for all purposes.

1. Pasut, G. and Veronese, M. (2012) State of the Art in Pegylation: The Great Versatility Achieved After Forty Years of Research. *J. Controlled Release* 161, 461-472.
2. Parveen, S. and Sahoo, S. K. Nanomedicine: Clinical Applications of Polyethylene Glycol Conjugated to Proteins and Drugs *Clin. Pharmacokinet.* 45, 965-988.
3. Alconcel, S. N. S., Baas, A. S. and Maynard, H. D. (2011) FDA-Approved Poly(ethylene glycol)-Protein Conjugate Drugs. *Polymer Chemistry* 2, 1442-1448.
4. Kling, J. (2013) Pegylation of Biologics: A Multipurpose Solution. *Bioprocess International* 11, 35-43.
5. Sustarsic, E. G., Junnila, R. K., and Kopchick, J. J. (2013) "Human Metastatic Melanoma Cell Lines Express High Levels of Growth Hormone Receptor and Respond to GH Treatment" *Biochem Biophys Res Commun.* 441: 144-150.
6. Basu, R., Wu, S., and Kopchick, J. J. (2017-1) "Targeting Growth Hormone Receptor in Human Melanoma Cells Attenuates Tumor Progression and Epithelial Mesenchymal Transition Via Suppression of Multiple Oncogenic Pathways" *Oncotarget* 8, 21579-21598.
7. Basu, R., Baumgaertel, N., Wu, S., and Kopchick, J. J. (2017-2) "Growth Hormone Receptor Knockdown Sensitizes Human Melanoma Cells to Chemotherapy by Attenuating Expression of ABC Drug Efflux Pumps" *Horm. Canc.* 8, 143-156.
8. Xu, J., Sun, D., Jiang, J., Deng., L., Zhang, Y., Yu, H., Bahl, D., Langenheim, J. F., Chen, W. Y., Fuchs, S. Y., and Frank, S. J. (2013) "The Role of Prolactin Receptor in GH Signaling in Breast Cancer Cells" *Mol. Endocrinol,* 27, 266-279.
9. Goffin, V., Bernichtein, S., Carriere, O., Bennet, W. F., Kopchick, J. J., and Kelly, P. A. (1999) *Endocrinology* 140, 3853-3856.
10. Kopchick, J. J., List, E. O., Kelder, B., Gosney, E. S., and Berryman, D. E. (2014) "Evaluation of growth hormone (GH) action in mice: Discovery of hGH receptor antagonists and clinical indications *Molecular and Cellular Endocrinology* 386, 34-45.
11. Pradhananga, S., Wilkinson, I., and Ross, R. J. M. (2002) "Pegvisomant: Structure and Function" *Journal of Molecular Endocrinology* 29, 11-14.

What is claimed:

1. A method for treating diseases or conditions responsive to human growth hormone receptor antagonists, comprising administering to the patient an effective amount of a human growth hormone receptor antagonist, comprising:

(a) human growth hormone receptor antagonist G120K having a DNA sequence of SEQ ID NO: 3 and an amino acid sequence of SEQ ID NO: 4, wherein two amino acids of human growth hormone receptor antagonist G120K have been mutated to cysteine, wherein the two amino acids mutated to cysteine are T142 and H151; and (b) a polyethylene glycol molecule conjugated to each substituted cysteine in the human growth hormone receptor antagonist G120K mutant, wherein the polyethylene glycol molecules conjugated to the two amino acids mutated to cysteine are two 4.5 kDa branched polyethylene glycols each containing three carboxylate anions, wherein the polyethylene glycol molecule is prepared by step-wise organic chemistry and is a substantially pure single compound, and wherein the polyethylene glycol molecule is a branched structure.

2. The method of claim 1, wherein the diseases or conditions are cancers that express high levels of the growth hormone receptor; high levels of the prolactin receptor; or high levels of both the growth hormone receptor and the prolactin receptor.

3. The method of claim 2, wherein the cancers are breast cancer, central nervous system cancer, melanoma, non-small cell lung cancer, ovarian cancer, prostate cancer, and renal cancer.

4. The method of claim 1, wherein the following amino acids mutations have been made to the human growth hormone receptor antagonist: H18D, H21N, R167N, K168A, D171S, K172R, E174S, and I179T, and wherein these mutations are operative to prevent binding to a prolactin receptor.

5. The method of claim 1, wherein the polyethylene glycol molecule in the human growth hormone antagonist contains a maleimide group for conjugation to a free sulfhydryl group.

6. The method of claim 1, wherein the human growth hormone receptor antagonist is encoded by a DNA having the sequence consisting of SEQ ID NO: 23.

7. The method of claim 1, wherein the human growth hormone receptor antagonist has an amino acid sequence consisting of SEQ ID NO: 24.

* * * * *